United States Patent
Tabata et al.

(10) Patent No.: US 12,414,676 B2
(45) Date of Patent: Sep. 16, 2025

(54) LIGHT SOURCE DEVICE

(71) Applicant: OLYMPUS CORPORATION, Tokyo (JP)

(72) Inventors: Motoki Tabata, Akishima (JP); Kazunari Hanano, Hachioji (JP); Kazuaki Murayama, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 756 days.

(21) Appl. No.: 17/546,352

(22) Filed: Dec. 9, 2021

(65) Prior Publication Data
US 2022/0095895 A1 Mar. 31, 2022

Related U.S. Application Data

(63) Continuation-in-part of application No. PCT/JP2019/024793, filed on Jun. 21, 2019.

(51) Int. Cl.
*A61B 1/00* (2006.01)
*A61B 1/07* (2006.01)
(Continued)

(52) U.S. Cl.
CPC ............ *A61B 1/00096* (2013.01); *A61B 1/07* (2013.01); *G02B 6/0025* (2013.01); *G02B 19/0052* (2013.01); *G02B 23/2469* (2013.01)

(58) Field of Classification Search
CPC . A61B 1/00165; A61B 1/0607; A61B 1/0615; A61B 1/0625; A61B 1/0684; A61B 1/07; A61B 1/0661; A61B 1/0669; A61B 1/0096; G02B 19/0052; G02B 6/0005–001; G02B 23/2469
See application file for complete search history.

(56) References Cited

U.S. PATENT DOCUMENTS

2014/0005483 A1* 1/2014 Ohashi .................. A61B 1/0646
600/162
2017/0168313 A1* 6/2017 Yamada ............... G02B 27/123

FOREIGN PATENT DOCUMENTS

CN 108027115 A 5/2018
JP 04-326306 A 11/1992
(Continued)

OTHER PUBLICATIONS

International Search Report dated Sep. 10, 2019 received in PCT/JP2019/024793.

*Primary Examiner* — Mariceli Santiago
(74) *Attorney, Agent, or Firm* — Scully, Scott, Murphy & Presser, P.C.

(57) ABSTRACT

A light source device includes: a plurality of first semiconductor light sources; a condenser lens; and a light guide having a prismatic shape in which an incident surface is on a first side of a central axis direction of the prismatic shape and an emission surface is on a second side of the central axis direction of the prismatic shape, a positional relationship between the plurality of first semiconductor light sources, the condenser lens, and the light guide is set such that a traveling direction of the light incident on the incident surface from the first semiconductor light sources via the condenser lens is perpendicular to a reflecting surface of the light guide in a plan view as viewed in the central axis direction of the prismatic shape, the incident light being reflected on the reflecting surface in the light guide.

20 Claims, 21 Drawing Sheets

(51) Int. Cl.
*F21V 8/00* (2006.01)
*G02B 19/00* (2006.01)
*G02B 23/24* (2006.01)

(56) References Cited

FOREIGN PATENT DOCUMENTS

| | | | | | |
|---|---|---|---|---|---|
| JP | 2004248834 | A | * | 9/2004 | |
| JP | 2013-244291 | A | | 12/2013 | |
| JP | 2015040892 | A | | 3/2015 | |
| JP | 2015132665 | A | | 7/2015 | |
| JP | 2016179009 | A | * | 10/2016 | ......... A61B 1/00117 |
| WO | WO-2016002025 | A1 | * | 1/2016 | ......... G02B 19/0019 |

* cited by examiner

LIGHT SOURCE DEVICE

CROSS-REFERENCE TO RELATED APPLICATION

This application is a continuation-in-part of International Application No. PCT/JP2019/024793, filed on Jun. 21, 2019, the entire contents of which are incorporated herein by reference.

BACKGROUND

1. Technical Field

The present disclosure relates to a light source device.

2. Related Art

In the medical field, an endoscope system is used for observing the inside of a subject. In general, an endoscope inserts an elongated flexible insertion portion into a subject such as a patient, and illuminates the inside of the subject with illumination light supplied from a distal end of the insertion portion by a light source device. In the endoscope, reflected light of the illumination light is received by an imaging unit at the distal end of the insertion portion to capture an in-vivo image. The in-vivo image captured by the imaging unit of the endoscope is subjected to predetermined image processing in a processing device of the endoscope system, and then displayed on a display of the endoscope system. A user such as a doctor observes an organ of the subject based on the in-vivo image displayed on the display.

As the light source device that emits the illumination light, a light source device including a plurality of light sources arranged on concentric circles different from each other, and a cylindrical rod that makes illuminance of light emitted by each light source uniform is known (see, for example, JP 2004-248834 A). In JP 2004-248834 A, the light sources are arranged on each concentric circle, and light from each light source is mixed by a rod, so that the illuminance at the center of an effective irradiation range and the illuminance around the center are made uniform.

SUMMARY

In some embodiments, a light source device including: a plurality of first semiconductor light sources; a holder configured to hold the plurality of first semiconductor light sources; a condenser lens configured to condense light emitted from the plurality of first semiconductor light sources; and a light guide having a prismatic shape in which an incident surface is on a first side of a central axis direction of the prismatic shape and an emission surface is on a second side of the central axis direction of the prismatic shape, light condensed by the condenser lens being incident on the incident surface, the light guide guiding the light incident on the incident surface to the emission surface while reflecting the incident light in the light guide a plurality of times, a positional relationship between the plurality of first semiconductor light sources, the condenser lens, and the light guide is set such that a traveling direction of the light incident on the incident surface from the first semiconductor light sources via the condenser lens is perpendicular to a reflecting surface of the light guide in a plan view as viewed in the central axis direction of the prismatic shape, the incident light being reflected on the reflecting surface in the light guide.

In some embodiments, provided is a light guide method of guiding light incident on a light guide by the light guide having a prismatic shape in which an incident surface is on a first side of a central axis direction of the prismatic shape and an emission surface is on a second side of the central axis direction of the prismatic shape. The light guide method includes: emitting light from a light source; condensing and allowing by a condenser lens the light emitted from the light source to enter in a direction perpendicular to a reflecting surface that reflects the light in a plan view as viewed in the central axis direction of the prismatic shape of the light guide; and guiding the light incident on the incident surface to the emission surface by the light guide while reflecting the incident light in the light guide a plurality of times.

In some embodiments, a light source device includes: a semiconductor light source configured to emit light; a condenser lens configured to condense light emitted from the semiconductor light source; and a light guide including an incident surface on which light condensed by the condenser lens is incident and an emission surface facing the incident surface, the light guide guiding light from the incident surface to the emission surface, in a plan view as viewed in a central axis direction of the light guide, the condenser lens is configured to enter light in a direction perpendicular to a reflecting surface that is a side surface of the light guide when the incident surface and the emission surface are bottom surfaces of the light guide.

In some embodiments, provided is a light guide method of guiding light by a light guide that has an incident surface on which light is incident and an emission surface facing the incident surface, and guides light from the incident surface to the emission surface. The light guide method includes: emitting light from a light source; allowing by a condenser lens light to enter in a direction in which a traveling direction of incident light and a traveling direction of reflected light are perpendicular to each other with respect to a reflecting surface that is a side surface of the light guide when the incident surface and the emission surface are bottom surfaces of the light guide in a plan view as viewed in a central axis direction of the light guide; and guiding the light incident on the incident surface to the emission surface by the light guide while reflecting the incident light in the light guide a plurality or times.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
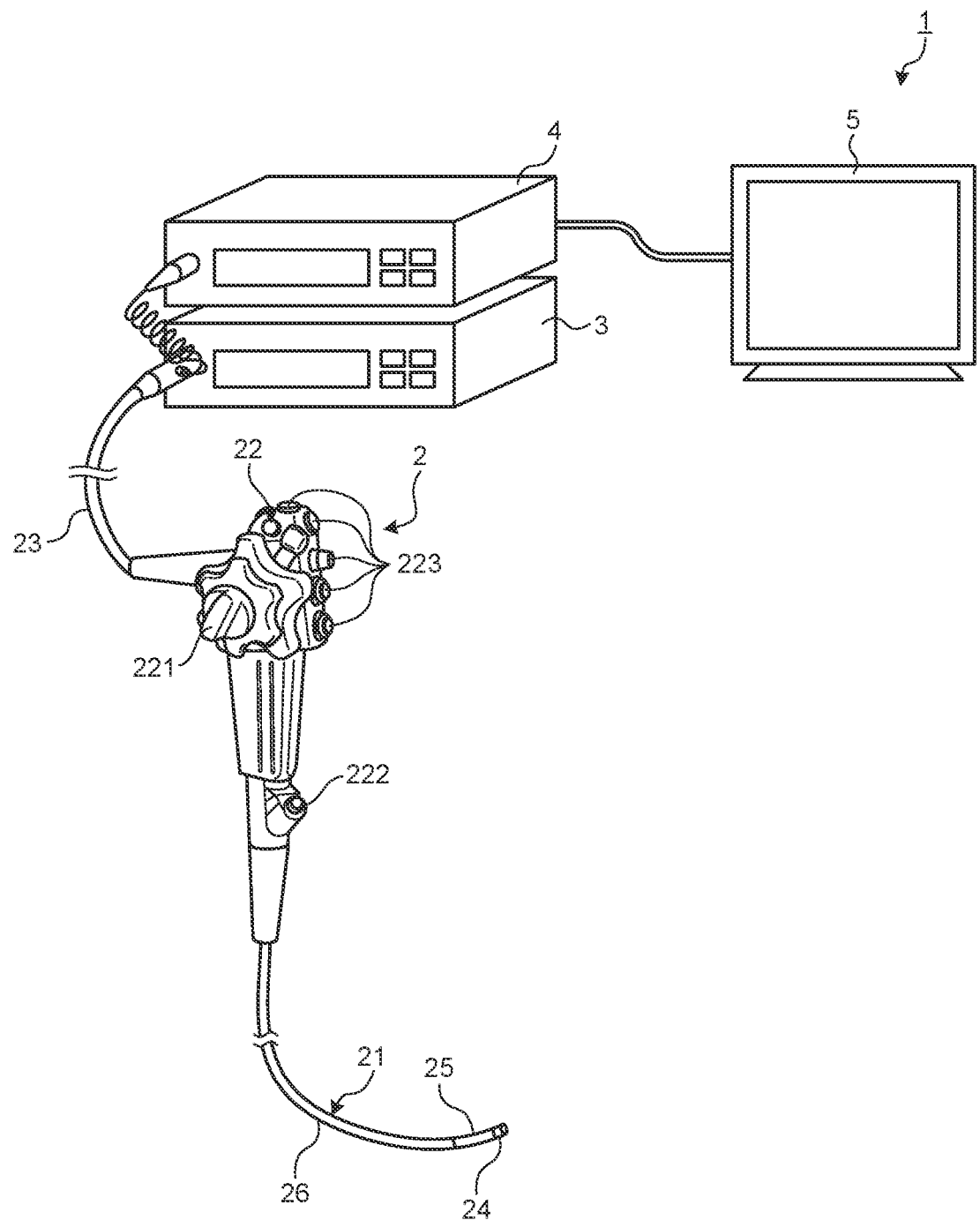
FIG. 1 is a diagram illustrating a schematic configuration of an endoscope system according to a first embodiment of the disclosure.

Hereinafter, modes for carrying out the disclosure (hereinafter, referred to as "embodiments") will be described. In the embodiments, as an example of a system including a light source device according to the disclosure, a medical endoscope system that captures and displays an image in a subject such as a patient will be described. Furthermore, the disclosure is not limited by the embodiments. Moreover, in the description of the drawings, the same portions will be described with the same reference numerals.

First Embodiment

Figure 2:
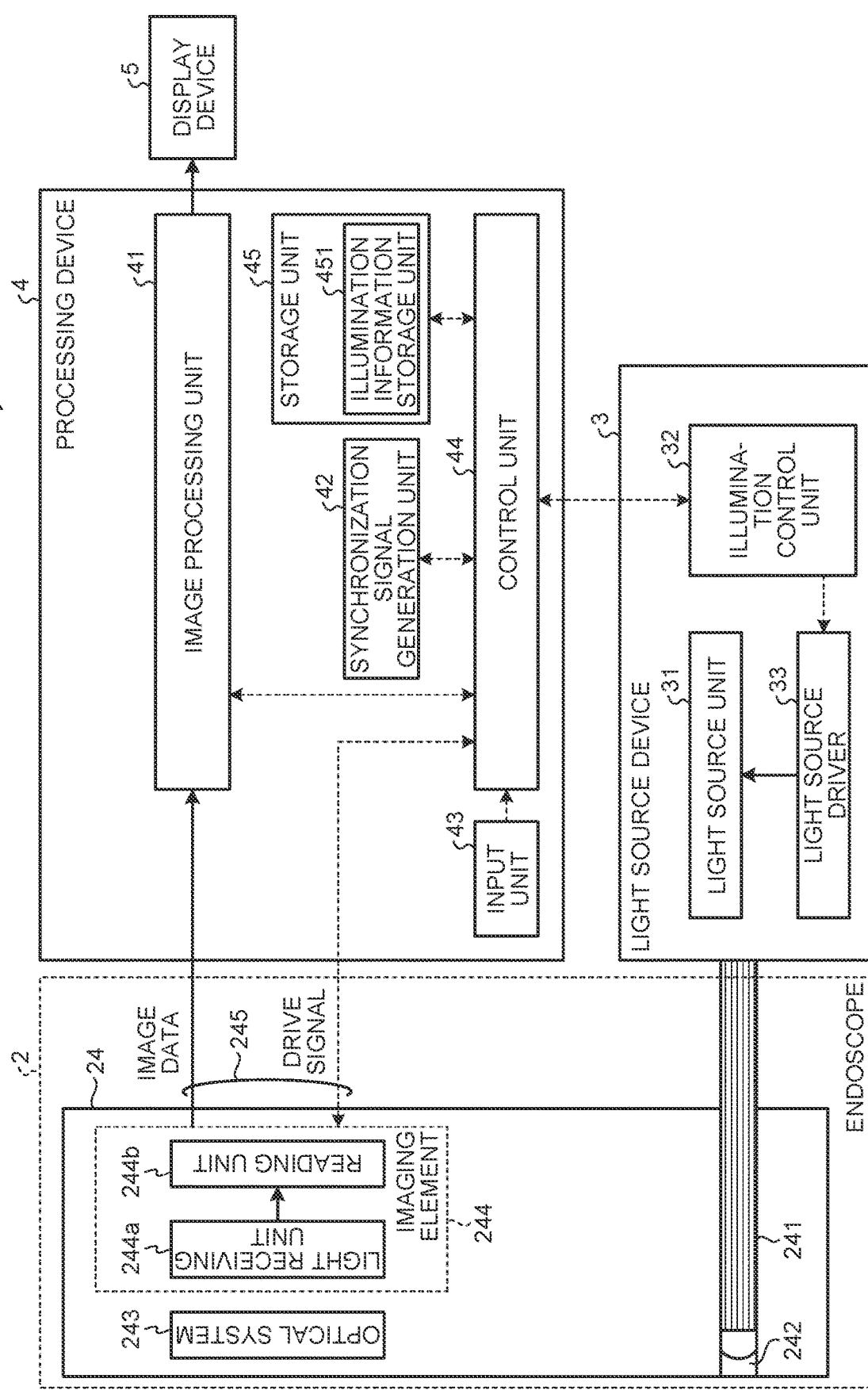
FIG. 2 is a block diagram illustrating a schematic configuration of the endoscope system according to the first embodiment of the disclosure.

FIG. 1 is a diagram illustrating a schematic configuration of an endoscope system according to a first embodiment of the disclosure. FIG. 2 is a block diagram illustrating a schematic configuration of the endoscope system according to the first embodiment.

An endoscope system 1 illustrated in FIGS. 1 and 2 includes an endoscope 2 that captures an in-vivo image of a subject by inserting a distal end portion into the subject, a light source device 3 that generates illumination light emitted from the distal end of the endoscope 2, a processing device 4 that performs predetermined signal processing on an imaging signal captured by the endoscope 2 and comprehensively controls an entire operation of the endoscope system 1, and a display device 5 that displays the in-vivo image generated by the signal processing of the processing device 4. Note that, in FIG. 2, transmission of a signal related to image data is indicated by a solid arrow, and transmission of a signal related to control is indicated by a broken arrow.

The endoscope 2 includes an insertion portion 21 having a flexible elongated shape, an operating unit 22 that is connected to a proximal end side of the insertion portion 21 and receives inputs of various operation signals, and a universal cord 23 that extends in a direction different from a direction in which the insertion portion 21 extends from the operating unit 22, and incorporates various cables connected to the light source device 3 and the processing device 4.

The insertion portion 21 includes a distal end portion 24 incorporating an imaging element 244 in which pixels that generate a signal by receiving light and performing photoelectric conversion are two-dimensionally arranged, a bendable curved portion 25 composed of a plurality of curved pieces, and a long flexible tube portion 26 connected to a proximal end side of the curved portion 25 and having flexibility. The insertion portion 21 is inserted into a body cavity of the subject and images an object by the imaging element 244, such as a living tissue at a position where external light does not reach.

The distal end portion 24 includes a light guide 241 configured using a plurality of glass fibers or the like and forming a light guide path of light emitted by the light source device 3, an illumination lens 242 provided at a distal end of the light guide 241, an optical system 243 for condensing, and the imaging element 244 (an imaging unit) provided at an image forming position of the optical system 243 and configured to receive light condensed by the optical system 243, photoelectrically convert the light into an electric signal, and perform predetermined signal processing.

The optical system 243 is configured using one or a plurality of lenses, and has an optical zoom function for changing an angle of view and a focus function for changing a focal point.

The imaging element 244 photoelectrically converts the light from the optical system 243 to generate an electric signal (image signal). Specifically, the imaging element 244 includes a light receiving unit 244a in which a plurality of pixels each including a photodiode that accumulates a charge according to a light amount, a capacitor that converts a charge transferred from the photodiode into a voltage level, and the like are arranged in a matrix, and each pixel photoelectrically converts the light from the optical system 243 to generate an electrical signal, and a reading unit 244b that sequentially reads the electric signal generated by a pixel arbitrarily set as a reading target among the plurality of pixels of the light receiving unit 244a and outputs the electric signal as an image signal. The imaging element 244 is realized by using, for example, a charge coupled device (CCD) image sensor or a complementary metal oxide semiconductor (CMOS) image sensor.

Note that the endoscope 2 includes a memory (not illustrated) that stores an execution program and a control program for the imaging element 244 to execute various operations, and data including identification information of the endoscope 2. The identification information includes unique information (ID) of the endoscope 2, a model year, specification information, a transmission method, and the like. Furthermore, the memory may temporarily store image data or the like generated by the imaging element 244.

The operating unit 22 includes a bending knob 221 that bends the curved portion 25 in a vertical direction and a horizontal direction, a treatment tool insertion unit 222 that inserts a treatment tool such as biopsy forceps, an electric scalpel, and an inspection probe into a body cavity of the subject, and a plurality of switches 223 that are operation input units that input operation instruction signals of peripheral devices such as an air supply unit, a water supply unit, and screen display control in addition to the processing device 4. The treatment tool inserted from the treatment tool insertion unit 222 comes out from an opening portion (not illustrated) via a treatment tool channel (not illustrated) of the distal end portion 24.

The universal cord 23 incorporates at least the light guide 241 and an assembly cable 245 including one or a plurality of signal lines. The assembly cable 245 includes a signal line for transmitting an imaging signal, a signal line for transmitting a drive signal for driving the imaging element 244, and a signal line for transmitting and receiving information including unique information regarding the endoscope 2 (imaging element 244). Note that, in the present embodiment, it is assumed that an electric signal is transmitted using a signal line, but an optical signal may be transmitted, or a signal may be transmitted between the endoscope 2 and the processing device 4 by wireless communication.

Next, a configuration of the light source device 3 will be described. The light source device 3 includes a light source unit 31, an illumination control unit 32, and a light source driver 33.

The light source unit 31 includes a plurality of light sources that emit, a plurality of illumination lights having different wavelength bands, a plurality of lenses, and the like, and emits the illumination lights including light of a predetermined wavelength band by driving each light source. The configuration of the light source unit 31 will be described later.

Based on a control signal (dimming signal) from a control unit 44, the illumination control unit 32 controls an amount of power to be supplied to each light source and controls drive timing of each light source included in the light source unit 31. In the first embodiment, the dimming signal is, for example, a pulse signal having a predetermined waveform.

Under the control of the illumination control unit 32, the light source driver 33 supplies a current to the light source unit 31 to cause each light source to emit light. In the light source unit 31, illumination light is emitted from one of the light sources, and the illumination light of a single color is emitted to the outside, or light is emitted from all the light sources, and white illumination light is emitted to the outside.

Figure 3:
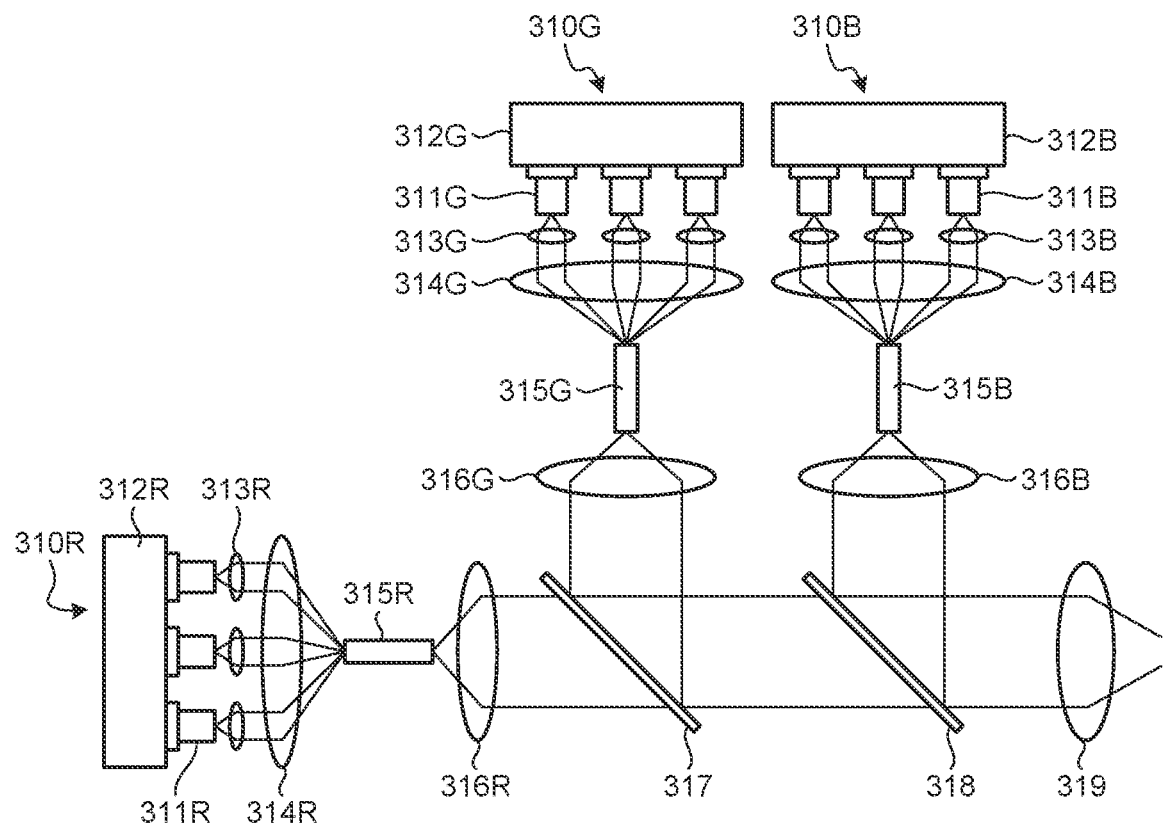
FIG. 3 is a diagram illustrating a configuration of a main portion of a light source device included in the endoscope system according to the first embodiment of the disclosure.

Here, the configuration of the light source unit 31 will be described with reference to FIGS. 3 and 4. FIG. 3 is a diagram illustrating a configuration of a main portion of a light source device included in the endoscope system according to the first embodiment of the disclosure. The light source unit 31 includes a first emission unit 310G, a second emission unit 310B, and a third emission unit 310F each provided with a plurality of light sources in the same arrangement.

Specifically, the light source unit 31 includes the first emission unit 310G that emits light in a wavelength band of 495 to 590 nm (green illumination light), the second emission unit 310B that emits light in a wavelength band of 390 to 495 nm (blue illumination light), and the third emission unit 310R that emits light in a wavelength band of 590 to 750 nm (red illumination light).

The first emission unit 310G includes a plurality of first light sources 311G that emit green illumination light, respectively. The plurality of first light sources 311G are arranged in a holder 312G.

The second emission unit 310B includes a plurality of second light sources 311B that emit blue illumination light, respectively. The plurality of second light sources 311B are disposed in a holder 312B.

The third emission unit 310R includes a plurality of third light sources 311R that emit red illumination light, respectively. The plurality of third light sources 311R are disposed in a holder 312R.

Each of the light sources included in the first emission unit 310G, the second emission unit 310B, and the third emission unit 310R is configured using a semiconductor laser (semiconductor light source).

Each emission unit (The first emission unit 310G, the second emission unit 310B, and the third emission unit 310R) includes, in addition to the light source and the holder, first lenses (first lenses 313G, 313B, 313R) that guide illumination light emitted from each light source, respectively, a condenser lens (condenser lenses 314G, 314B, 314R) that, condenses the illumination light passing through the first lenses, a rod (rod 315G, 315B, 315R) into which light condensed by the condenser lens is introduced and from which light having a uniform illuminance distribution is emitted, and a collimator lens (collimator lenses 316G, 316B, and 316R) that converts the light emitted from the rod into parallel light. In the present specification, the rod corresponds to a light guide.

The light source unit 31 further includes a dichroic mirror 317 that bends the light in the wavelength band emitted from the first emission unit 310G and transmits the light in the wavelength band of the light emitted from the third emission unit 310R, a dichroic mirror 318 that bends the light in the wavelength band emitted from the second emission unit 310B and transmits the light in the wavelength band of the light emitted from the first emission unit 310G and the third emission unit 310R, and a second lens 319 that guides the light passed through the dichroic mirror 318 or the light folded by the dichroic mirror 318 to the light guide 241. The dichroic mirrors 317 and 318 allow light incident from the collimator lens to pass therethrough or bend the light to change respective optical paths in directions traveling on the same optical axis.

Here, in the first emission unit 310G and the second emission unit 310B, an optical axis of an optical system including the first lens, the condenser lens, the rod, and the collimator lens is perpendicular to an optical axis of an optical system including the first lens, the condenser lens, the rod, and the collimator lens in the third emission unit 310R. Specifically, the optical axis of the third emission unit 310R is parallel to an optical axis of second lens 319, and the optical axes of the first emission unit 310G and the second emission unit 310B are perpendicular to the optical axis of the second lens 319.

Figure 4:
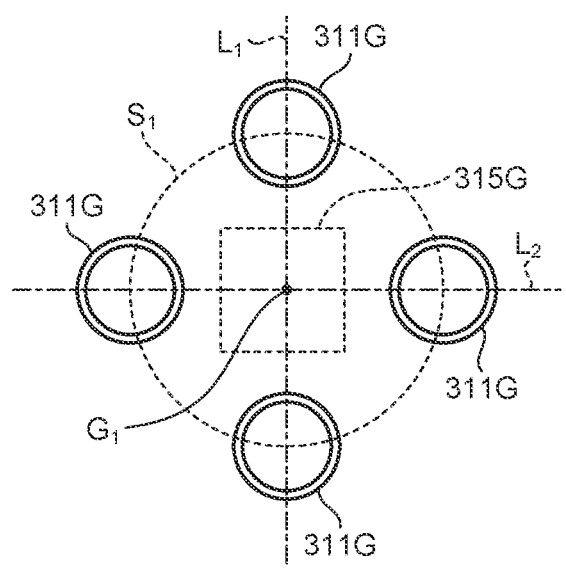
FIG. 4 is a diagram illustrating an arrangement, of light sources in the light source device included in the endoscope system according to the first embodiment of the disclosure.

FIG. 4 is a diagram illustrating an arrangement of light sources in the light source device included in the endoscope system according to the first embodiment of the disclosure. FIG. 4 illustrates the arrangement of the light sources in the first emission unit 310G. Note that the arrangement of the light sources with respect to the rod is the same for the second emission unit 310B and the third emission unit 310R.

In the first emission unit 310G, four first light sources 311G are provided. The four first light sources 311G are provided on the same surface of the holder 312G (see FIG. 3).

Here, the rod 315G extends in a prismatic shape, and an outer edge of a surface (an end surface and a cross section) orthogonal to the longitudinal direction is rectangular. In the first embodiment, a central axis (central axis $N_1$ to be described later) extending in the longitudinal direction of the rod 315G coincides with the optical axis of the optical system including the first lens 313G, the condenser lens 314G, the rod 315G, and the collimator lens 316G.

The four first light sources 311G are arranged around the rod 315G in a plan view (see FIG. 4) viewed in an optical axis direction from an end portion of the rod 315G on a side opposite to a side of the condenser lens 314G. Specifically, the four first light sources 311G are arranged at equal intervals on a circle $S_1$ centered on a center of gravity $G_1$ of an incident surface of the rod 315G in the above-described plan view. The diameter of the circle $S_1$ is set to be equal to or less than an effective diameter of the condenser lens 314G.

Furthermore, one of straight lines L1 and L2 passing through the center of gravity G1 of the rod 315G and orthogonal to each other passes through the four first light sources 311G. The straight, lines $L_1$ and $L_2$ pass through the center (center of gravity) of the first light sources 311G and are orthogonal to side surfaces, respectively, which intersect the straight line among side surfaces of the rod 315G. In the first embodiment, since the rod 315G has a prismatic shape extending with a uniform size (cross section), the center of gravity $G_1$ of the rod 315G coincides with the center of gravity of an incident surface (incident surface $P_1$ to be described later).

Further, the optical axis of each of the first light sources 311G is parallel to the longitudinal direction of the rod 315G. Note that the central axis (axis passing through the center of gravity $G_1$ and extending in the longitudinal direction) of the rod 315G coincides with the optical axis of the optical system including the rod.

Figure 5:
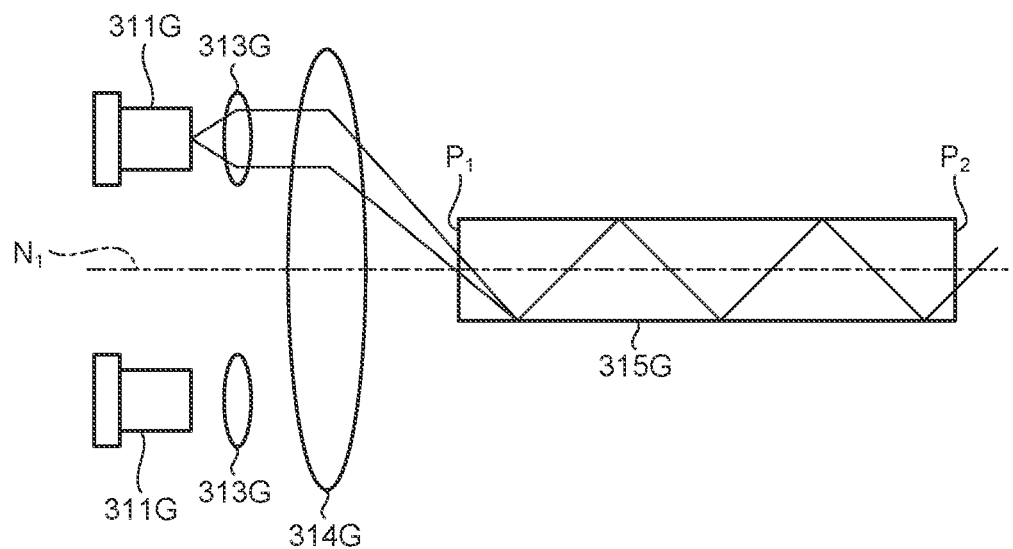
FIG. 5 is a diagram illustrating working of a rod in the light source device included in the endoscope system according to the first embodiment of the disclosure.
Figure 6:
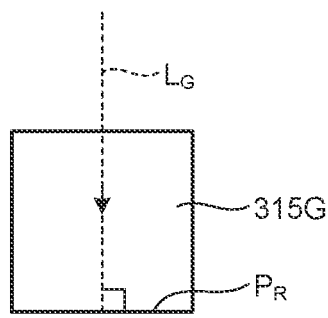
FIG. 6 is a diagram illustrating working of the rod in the light source device included in the endoscope system according to the first embodiment of the disclosure.

FIGS. 5 and 6 are diagrams for explaining the working of the rod in the light source device included in the endoscope system according to the first embodiment of the disclosure. FIG. 6 is a plan view of the rod 315G viewed in a direction of a central axis $N_1$ of the rod 315G illustrated in FIG. 5 from an end portion of the rod 315G on a side opposite to the side of the condenser lens 314G. In FIGS. 5 and 6, only a trajectory of light from one first light source 311G is illustrated as an example.

The light (green illumination light) emitted from the first light source 311G is incident on the condenser lens 314G via the first lens 313G. The light incident on the condenser lens 314G is bent and incident on the rod 315G (see FIG. 5). At this time, a traveling direction (an optical axis) of the light incident on the rod 315G is inclined with respect to the central axis $N_1$ of the rod 315G.

Here, the rod 315G has an incident surface $P_1$ on which light is incident at one end in a direction of the central axis $N_1$, and an emission surface $P_2$ from which light is emitted at the other end in the direction of the central axis $N_1$. In addition, the rod 315G has a prismatic shape in which the incident surface $P_1$ is one bottom surface and the emission surface $P_2$ is the other bottom surface. The central axis $N_1$ of the rod 315G passes through the center of gravity of the incident surface $P_1$ and the center of gravity of the emission surface $P_2$, respectively. The direction of the central axis $N_1$ corresponds to a height direction of the prismatic shape.

In addition, the traveling direction of the light $L_G$ incident on the rod 315G is perpendicular to a reflecting surface $P_R$ (here, corresponding to a boundary surface between the inside and the outside of the rod 315G) of the light $L_G$ in the rod 315G. The term "perpendicular" as used herein includes manufacturing errors and the like. That is, the perpendicular includes, for example, 90° and a deviation in a range of about 90°±3°.

The light incident on the rod 315G travels toward an end portion (a reflecting surface) of the rod 315G on a side opposite to incident side while being reflected in the rod 315G.

The light emitted from each of the first light sources 311G is incident on the rod 315G and is repeatedly reflected, whereby the light of each of the light sources is mixed, and light having a uniform light intensity distribution in the cross section of the rod 315G is generated. At this time, as the number of times of reflection of light by each light source increases, positional unevenness of the light intensity derived from a light source position is eliminated, and the effect of uniformizing the intensity distribution increases.

The light having the uniform intensity distribution enters the light guide 241 through the second lens 319. At this time, light of equivalent intensity is guided to each glass fiber of the light guide 241.

Next, a configuration of the processing device 4 will be described. The processing device 4 includes an image processing unit 41, a synchronization signal generation unit 42, an input unit 43, a control unit 44, and a storage unit 45.

The image processing unit 41 receives image data of the illumination light of each color imaged by the imaging element 244 from the endoscope 2. When receiving analog image data from the endoscope 2, the image processing unit 41 performs A/D conversion to generate a digital imaging signal. Furthermore, in a case where image data is received as an optical signal from the endoscope 2, the image processing unit 41 performs photoelectric conversion to generate digital image data.

The image processing unit 41 performs predetermined image processing on the image data received from the endoscope 2 to generate an image, and outputs the image to the display device 5. Here, the predetermined image processing includes synchronization processing, gradation correction processing, color correction processing, and the like. The synchronization processing is processing of synchronizing each of R image data based on image data generated by the imaging element 244 when the light source unit 31 emits R illumination light, G image data based on image data generated by the imaging element 244 when the light source unit 31 emits G illumination light, and B image data based on image data generated by the imaging element 244 when the light source unit 31 emits B illumination light. The gradation correction processing is processing of correcting gradation for image data. The color correction processing is processing of performing color tone correction on image data. The image processing unit 41 generates a processed imaging signal (hereinafter, it is also simply referred to as an imaging signal) including an in-vivo image generated by the above-described image processing. Note that the image processing unit 41 may perform gain adjustment according to the brightness of an image. The image processing unit 41 is configured using a general-purpose processor such as a central processing unit (CPU) or a dedicated processor such as various arithmetic circuits that execute specific functions, such as an application specific integrated circuit (ASIC).

Furthermore, the image processing unit 41 may include a frame memory that holds R image data, G image data, and B image data.

The synchronization signal generation unit 42 generates a clock signal (synchronization signal) serving as a reference of an operation of the processing device 4, and outputs the generated synchronization signal to the light source device 3, the image processing unit 41, the control unit 44, and the endoscope 2. Here, the synchronization signal generated by the synchronization signal generation unit 42 includes a horizontal synchronization signal and a vertical synchronization signal.

Therefore, the light source device 3, the image processing unit 41, the control unit 44, and the endoscope 2 operate in synchronization with each other by the generated synchronization signal.

The input unit 43 is realized by using a keyboard, a mouse, a switch, and a touch panel, and receives inputs of various signals such as an operation instruction signal that instructs an operation of the endoscope system 1. Note that the input unit 43 may include a switch provided in the operating unit 22 or a portable terminal such as an external tablet computer.

The control unit 44 performs drive control of each component including the imaging element 244 and the light source device 3, input/output control of information with respect to each component, and the like. The control unit 44 refers to control information data (for example, a reading timing or the like) for imaging control stored in the storage unit 45, and transmits the control information data as a drive signal to the imaging element 244 via a predetermined signal line included in the assembly cable 245. Furthermore, the control unit 44 causes the illumination control unit 32 to control the light source unit with reference to the control information data for light source control stored in the storage unit 45. The control unit 44 is configured using a general-purpose processor such as a CPU or a dedicated processor such as various arithmetic circuits that execute specific functions, such as an ASIC.

The storage unit 45 stores various programs for operating the endoscope system 1, and data including various parameters and the like necessary for the operation of the endoscope system 1. Furthermore, the storage unit 45 stores identification information of the processing device 4. Here, the identification information includes unique information (ID), a year of manufacture, specification information, and the like of the processing device 4. In addition, the storage unit 45 includes an illumination information storage unit 451 that stores information regarding the arrangement and the like of the light sources included in the light source device 3. The illumination information storage unit 451 stores, for example, a set light amount (in this case, a light amount of illumination light emitted by the light source device 3), a light emission condition of the light sources according to a light emitting order of the light sources (for example, a light source light emitting order of RGB), and the like.

Furthermore, the storage unit 45 stores various programs including an image acquisition processing program for executing an image acquisition processing method of the processing device 4. The various programs can be recorded on a computer-readable recording medium such as a hard disk, a flash memory, a CD-ROM, a DVD-ROM, or a flexible disk, and widely distributed. Note that the above-described various programs can also be acquired by being downloaded via a communication network. The communication network here is realized by, for example, an existing public line network, a local area network (LAN), a wide area network (WAN), or the like, and may be wired or wireless.

The storage unit 45 having the above configuration is realized using a read only memory (ROM) in which the various programs and the like are installed in advance, a RAM, a hard disk, and the like that store calculation parameters, data, and the like of each processing.

The display device 5 displays a display image corresponding to the image signal received from the processing device 4 (image processing unit 41) via a video cable. The display device 5 is configured using a monitor such as liquid crystal or organic electro luminescence (EL).

In the first embodiment described above, a plurality of light sources (for example, the first light sources 311G illustrated in FIG. 4) are arranged at positions that are provided around the rod and allow light to enter in a direction perpendicular to the reflecting surface in the rod (for example, the reflecting surface $P_R$ in the rod 315G) in a plan view in the direction of the central axis of the rod (for example, the central axis $N_1$ illustrated in FIG. 5). According to the present first embodiment, since the light emitted from each light source is incident to incline with respect to the central axis of the rod, and is mixed by repeating reflection in the rod a plurality of times, it is possible to uniformly mix the light from the plurality of light sources and emit the light in which the positional unevenness of the light intensity is suppressed. As a result, the illuminance at the center of an effective irradiation range and the illuminance around the center are reliably uniformized, and an object can be irradiated with light in which the illuminance unevenness is suppressed.

Here, in the first embodiment, an example in which the rod has a prismatic shape has been described, but for example, in a case where the rod has a cylindrical shape, since the reflecting surface of light has a curved surface, spread of the reflected light is suppressed, and the uniformizing effect is lower than that of the prismatic shape. Therefore, it is preferable that the rod has a prismatic shape and the reflecting surface of light is a flat surface.

Modification of First Embodiment

Figure 7:
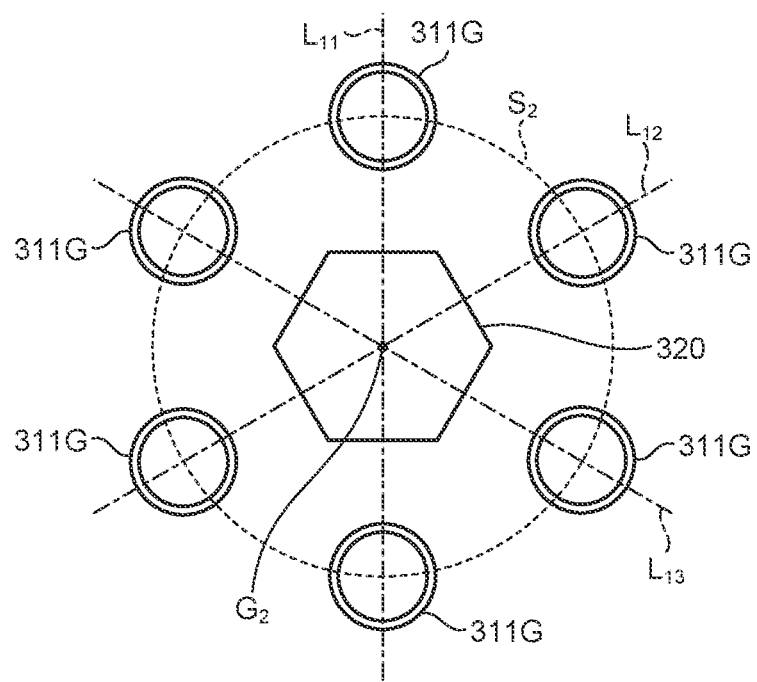
FIG. 7 is a diagram illustrating a configuration of a main portion of a light source device according to a modification of the first embodiment of the disclosure.

Next, a modification of the first embodiment of the disclosure will be described with reference to FIG. 7. FIG. 7 is a diagram illustrating a configuration of a main portion of a light source device according to the modification of the first embodiment of the disclosure. An endoscope system according to the present first modification has the same configuration except that the number (arrangement) of the rods and the light sources in the light source device 3 of the endoscope system 1 described above is changed. Hereinafter, a configuration of a main portion of a light source device different from the above-described first embodiment will be described. Hereinafter, the configuration of a first emission unit (corresponding to the first emission unit 310G described above) will be described, but similar configurations can be adopted for a second emission unit and a third emission unit as in the first embodiment.

The first emission unit according to the present modification includes six first light sources 311G, first lenses 313G that guide illumination light emitted from the respective light sources, respectively, a condenser lens 314G that condenses the illumination light passing through the first lenses 313G, a rod 320 into which light condensed by the condenser lens 314G is introduced and from which light having a uniform illuminance distribution is emitted, and a collimator lens 316G that converts the light emitted from the rod 320 into parallel light. The configuration of the first light sources 311G, and the first lenses 313G, the condenser lens 314G, and the collimator lens 316G are similar to those of the first embodiment described above.

The rod 320 has a prismatic shape having an incident surface at one end in a longitudinal direction and an emission surface at the other end, and an outer edge of a surface (an end surface and a cross section) orthogonal to the longitudinal direction has a hexagonal shape. In the present modification, the central axis extending in the longitudinal direction of the rod 320 coincides with the optical axis of the optical system including the first lenses 313G, the condenser lens 314G, the rod 320, and the collimator lens 316G.

The six first light sources 311G are arranged around the rod 320 in a plan view (see FIG. 7) viewed in an optical axis direction from an end portion of the rod 320 on a side opposite to the side of the condenser lens 314G. Specifically, the six first light sources 311G are arranged at equal intervals on a circle $S_2$ centered on a center of gravity $G_2$ of the rod 320 in the above-described plan view. Furthermore, one of straight lines $L_{11}$, $L_{12}$, and $L_{13}$ passing through the center of gravity $G_2$ of the rod 320G and intersecting one another passes through the six first light sources 311G. The straight lines $L_{11}$, $L_{12}$, and $L_{13}$ pass through the center (the center of gravity of the incident surface) of the first light sources 311G and are orthogonal to side surfaces, respectively, which intersect the straight line among side surfaces of the rod 320.

Furthermore, the optical axis of each of the first light sources 311G is parallel to the longitudinal direction of the rod 320. Note that the central axis (axis passing through the center of gravity $G_2$ and extending in the longitudinal direction) of the rod 320 coincides with the optical axis of the optical system including the rod.

The light (green illumination light) emitted from the first light sources 311G is incident on the condenser lens 314G via the first lenses 313G. The light incident on the condenser lens 314G is bent and incident on the rod 320 (see, for example, FIG. 5). At this time, the traveling direction (optical axis) of the light incident on the rod 320 is inclined with respect to the central axis of the rod 320. In addition, the traveling direction of the light incident on the rod 320 is perpendicular to the light reflecting surface (here, corresponding to the boundary surface between the inside and the outside of the rod 320) of the rod 320.

The light incident on the rod 320 travels toward an end portion of the rod 320 on a side opposite to incident side while being reflected in the rod 320. The light emitted from each of the first light sources 311G is incident on the rod 320 and is repeatedly reflected, whereby the light of each of the light sources is mixed, and light having a uniform light intensity distribution in the cross section of the red 320 is generated.

In the modification described above, a plurality of light sources are arranged at positions that are provided around the rod 320 and allow light to enter in a direction perpendicular to a reflecting surface in the rod (for example, a reflecting surface in the rod 320) in a plan view as viewed in the central axis direction of the rod. According to the present modification, since the light emitted from each light source is incident to incline with respect to the central axis of the rod and is mixed by repeating reflection in the rod a plurality of times, it is possible to uniformly mix the light from the plurality of light sources and emit the light with suppressed illuminance unevenness. As a result, the illuminance at the center of the effective irradiation range and the illuminance around the center are more reliably uniformized, and an object can be irradiated with light in which the illuminance unevenness is suppressed.

In addition to the hexagonal rod shown in the modification described above, any polygonal shape having an even number of vertices can be applied.

Second Embodiment

Figure 8:
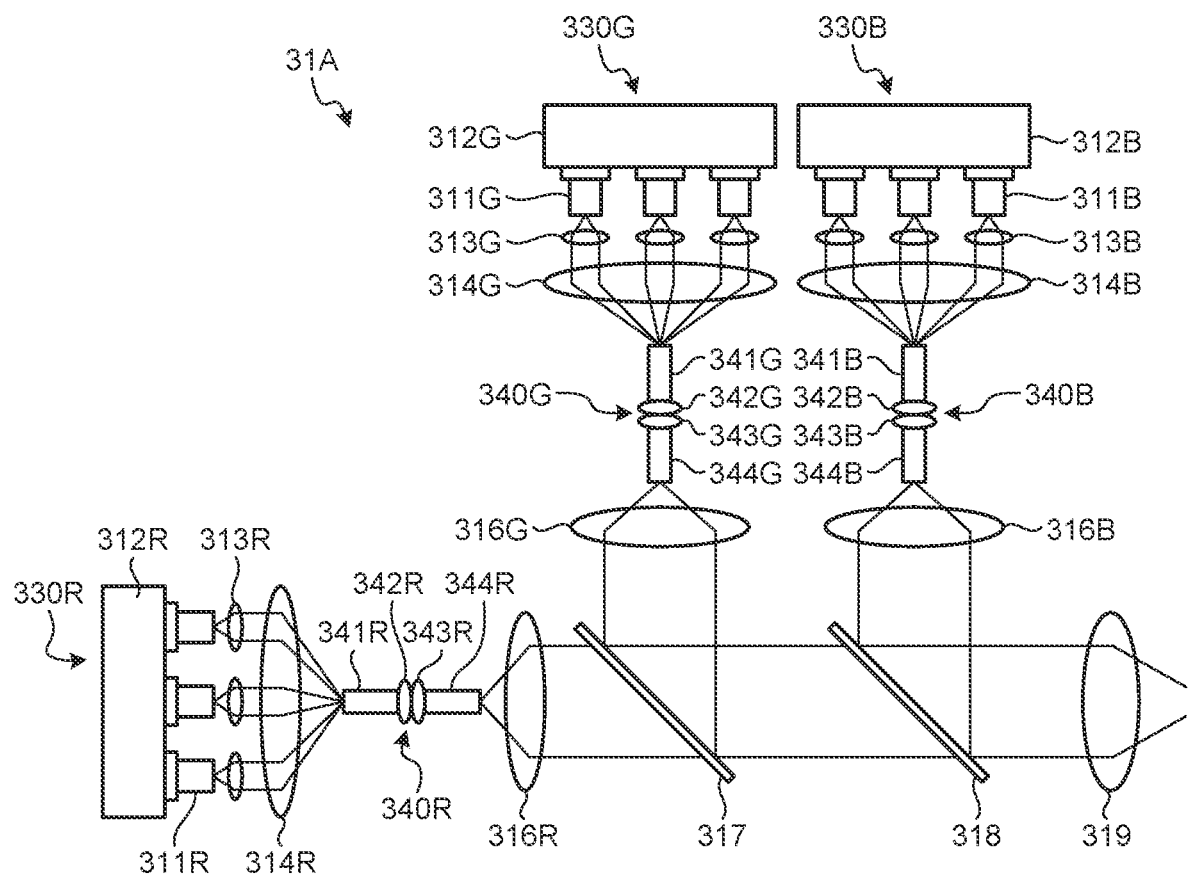
FIG. 8 is a diagram illustrating a configuration of a main portion of a light source device according to a second embodiment of the disclosure.

Next, a second embodiment of the disclosure will be described with reference to FIG. 8. FIG. 8 is a diagram illustrating a configuration of a main portion of a light source device according to the second embodiment of the disclosure. The endoscope system according to the present second embodiment has the same configuration except that the configuration of the light source unit in the light source device 3 of the endoscope system 1 described above is changed. Hereinafter, a configuration of a main portion (light source unit 31A) of a light source device different from the above-described first embodiment will be described.

The light source unit 31A according to the present second embodiment includes a first emission unit 330G, a second emission unit 330B, and a third emission unit 33GR.

Specifically, the light source unit 31A includes the first emission unit 330G that emits green illumination light, the second emission unit 330B that emits blue illumination light, and the third emission unit 330R that emits red illumination light.

Each emission unit (the first emission unit 330G, the second emission unit 330B, and the third emission unit 330R) includes a plurality of light sources (first light sources 311G, second light sources 311B, third light sources 311R), a holder (holders 312G, 312B, 312R) in which each light source is arranged, first lenses (first lenses 313G, 313B, 313R) that guide illumination light emitted from each light source, respectively, a condenser lens (condenser lenses 314G, 314B, 314R) that collects the illumination light passing through the first lenses, a rod (rod 340G, 340B, 340R) into which light collected by the condenser lens is introduced and from which light having a uniform illuminance distribution is emitted, and a collimator lens (collimator lenses 316G, 316B, and 316R) that converts the light emitted from the rod into parallel light.

Furthermore, the light source unit 31A includes the dichroic mirror 317, the dichroic mirror 318, and the second lens 319 described above.

Here, since the configuration other than the rod is the same as that of the first embodiment described above, the description thereof will be omitted. Hereinafter, a rod having a configuration different from that of the first embodiment will be described.

The rod (rod 340G, 340B, 340R) includes a first rod (first rod 341G, 341B, 341R) into which the light condensed by the condenser lens is introduced, conversion lenses (conversion lenses 342G, 342B, 342R, 343G, 343B, 343R) that convert an angular component into a position component in the light emitted from the first rod, and a second rod (second rod 344G, 344B, 344R) on which the light passing through the conversion lenses is incident. Hereinafter, the configuration of the first emission unit 330G will be described as an example, but the same applies to the second emission unit 330B and the third emission unit 330R.

Each of the first rod 341G and the second rod 344G has a prismatic shape having an incident surface at one end in the longitudinal direction and a reflecting surface at the other end, and an outer edge of a surface (an end surface and a cross section) of each of the first rod 341G and the second rod 344G orthogonal to the longitudinal direction is rectangular. The central axis extending in the longitudinal direction of the first rod 341G and the second rod 344G coincides with the optical axis of the optical system including the first lenses 313G, the condenser lens 314G, the rod 340G, and the collimator lens 316G of each emission portion. Note that the arrangement of the first light sources 311G with respect to the first rod 341G and the second rod 344G is similar to that in the first embodiment.

The light emitted from the light sources enters the condenser lens 314G via the first lenses 313G. The light incident on the condenser lens 314G is bent and incident on the rod 340G. At this time, a traveling direction (an optical axis) of the light incident on the rod 340G is inclined with respect to the central axis of the rod 340G. In addition, the traveling direction of the light incident on the rod 340G is perpendicular to the light reflecting surface (here, corresponding to the boundary surface between the inside and the outside of the rod 340G) of the rod 340G.

The light incident on the rod 340G travels toward an end portion of the first rod 341G on a side opposite to incident side while being reflected in the first rod 341G. Specifically, for example, in the first emission unit 33CG, the light from the condenser lens 314G is incident on the first rod 341G. The light is incident on the first rod 341G and repeatedly reflected, whereby the light of each of the first light sources 311G is mixed, and the light in which the positional unevenness is eliminated is generated.

Thereafter, light from the first rod 341G is incident on the conversion lenses 342G and 343G. The conversion lenses 342G and 343G generate light obtained by converting angle components of light having incident angles different from each other into position components.

The light incident on the second rod 344G through the conversion lens 343G travels toward an end portion of the second rod 344G on a side opposite to incident side while being reflected in the second rod 344G. The light is incident on the second rod 344G and repeatedly reflected, whereby the light of each of the first light sources 311G is mixed. At this time, since the angle components are converted into the position components by the conversion lenses 342G and 343G, the light in which angle unevenness and positional unevenness are suppressed is generated.

In the second embodiment described above, as in the first embodiment, a plurality of light sources are arranged at positions that are provided around the rod and allow light to enter in a direction perpendicular to the reflecting surface in the rod (for example, the reflecting surface of the first rod 341G or the reflecting surface of the second rod 344G) in a plan view as viewed in the central axis direction of the rod. According to the present second embodiment, since the light emitted from each light source is incident to incline with respect to the central axis of the rod and is mixed by repeating reflection in the rod a plurality of times, it is possible to uniformly mix the light from the plurality of light sources and emit the light with suppressed illuminance unevenness. As a result, the illuminance at the center of the effective irradiation range and the illuminance around the center are more reliably uniformized, and an object can be irradiated with light in which the illuminance unevenness is suppressed.

Further, in the second embodiment, after the positional unevenness is eliminated by the first rod, the angular component is converted into the positional component by the conversion lenses, and the positional unevenness is suppressed again by the second rod. According to the present second embodiment, since the angle components are converted into the position components to suppress angle unevenness, and the positional unevenness is suppressed by the first rod and the second rod, the angle unevenness can also be uniformized, and the light in which the unevenness is suppressed can be emitted with higher accuracy. As a result, it is possible to irradiate an object with light in which the illuminance at the center of the effective irradiation range and the illuminance around the center are made uniform more reliably.

Third Embodiment

Figure 9:
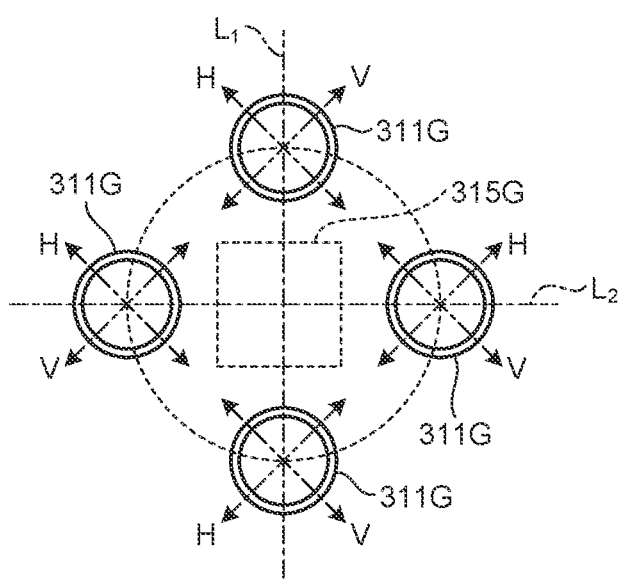
FIG. 9 is a diagram illustrating an arrangement of light sources in a light source device included in an endoscope system according to a third embodiment of the disclosure.

Next, a third embodiment of the disclosure will be described with reference to FIGS. 9 to 11. FIG. 9 is a diagram illustrating an arrangement of light sources in a light source device included in an endoscope system according to the third embodiment of the disclosure. The endoscope system according to the present third embodiment has the same configuration as that of the first embodiment described above. Hereinafter, portions different from the above-described first embodiment will be described. Hereinafter, the configuration of a main portion of the first emission unit 310G will be described, but the second emission unit 310B and the third emission unit 310R can be similarly configured.

A light source including a semiconductor laser generally has an elliptical light distribution on an emission surface. Therefore, light emitted from the light source also has an elliptical light distribution. For example, in each light source (here, the first light source 311G), an irradiation range is different between an H direction corresponding to a major axis direction of an ellipse in the light distribution and a V direction corresponding to a minor axis direction.

Figure 10:
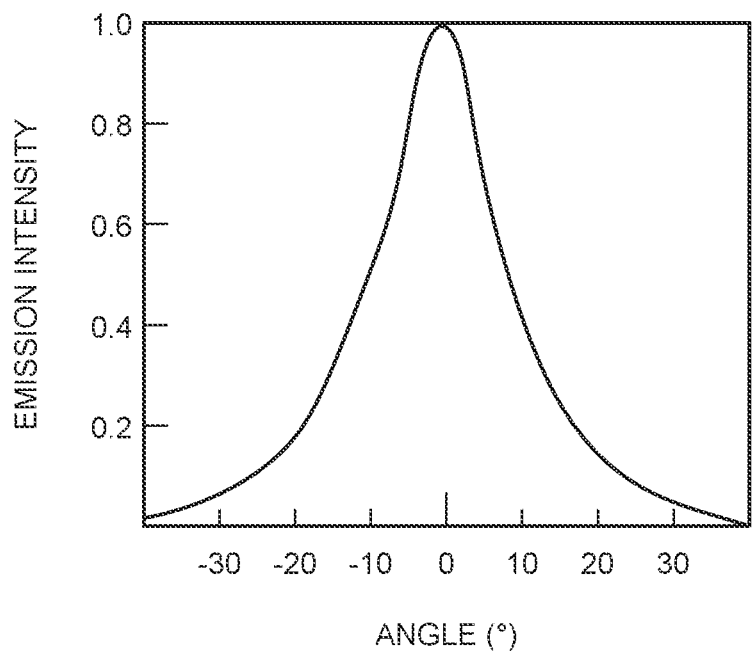
FIG. 10 is a diagram illustrating an emission intensity distribution of the light source in the light source device according to the third embodiment of the disclosure.
Figure 11:
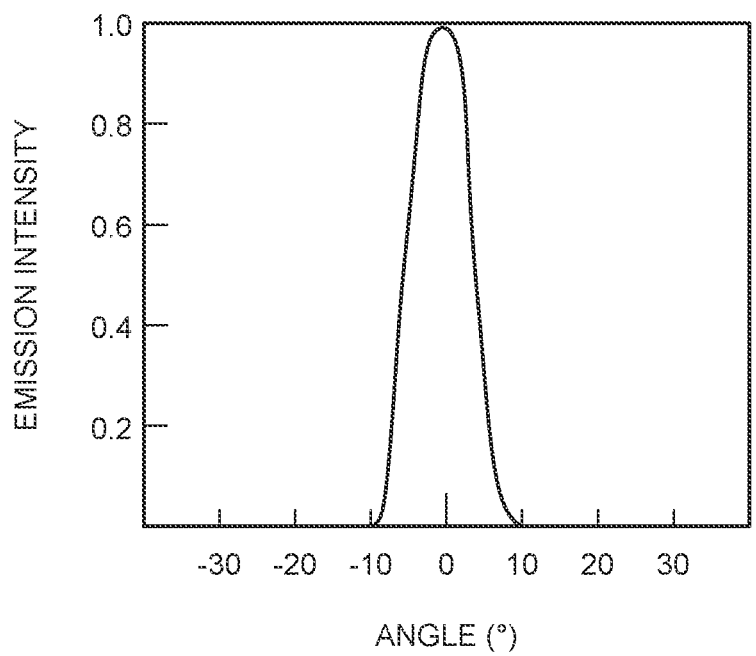
FIG. 11 is a diagram illustrating an emission intensity distribution of the light source in the light source device according to the third embodiment of the disclosure.

FIGS. 10 and 11 are diagrams illustrating an emission intensity distribution of the light source in the light source device according to the third embodiment of the disclosure. FIG. 10 illustrates a light distribution in the H direction corresponding to the major axis direction of the ellipse. FIG. 11 illustrates a light distribution in the V direction corresponding to the minor axis direction of the ellipse. In FIGS. 10 and 11, the center of the light source (the center of an emission portion of light) is set to 0°, and an emission intensity of light traveling at an angle inclined with respect to the optical axis passing through the central axis is illustrated. Note that an angle on a side arbitrarily set with respect to the center is positive, and an opposite side is negative.

In both of light distributions in the H direction and the V direction, the emission intensity decreases as the angle increases. An emission range in the light distribution in the H direction (a range in which the emission intensity is larger than 0) is larger than the emission range in the light distribution in the V direction. That is, light is irradiated to a wider range in the H direction than in the V direction. In a light source using a semiconductor laser, an irradiation range and a light intensity vary depending on the H direction and the V direction described above.

In the present third embodiment, the two first light sources 311G facing across the rod 315G from one another are arranged such that the H directions (V direction) of the two first light sources 311G are perpendicular to each other. For example, in FIG. 9, in the first light source 311G located above and below the rod 315G, the H direction (V direction) faces directions perpendicular to each other.

In addition, in order to suppress unevenness caused by the difference in the light distributions in the H direction and the V direction, for example, the H direction and the V direction of each light source preferably form 45° with respect to a straight line passing through the center of gravity $G_1$ of the rod 315G and passing through itself among the straight lines $L_1$ and $L_2$ orthogonal to each other.

According to the present third embodiment, in addition to the effects of the first embodiment described above, by arranging the two first light sources 311G facing across the rod 315G from one another in a plan view as viewed in the central axis direction of the rod such that the H directions (V directions) of the two first light sources 311G are perpendicular to each other in the plan view as viewed in the central axis direction of the rod, the difference in the light distributions in the H direction and the V direction described above can be reduced, and unevenness in the light distribution can be suppressed.

Fourth Embodiment

Figure 12:
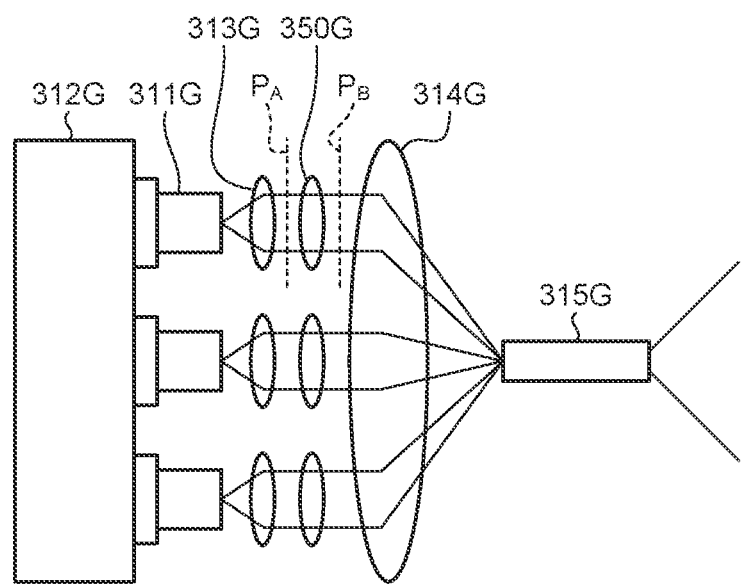
FIG. 12 is a diagram illustrating a configuration of a main portion of a light source device according to a fourth embodiment of the disclosure.

Next, a fourth embodiment of the disclosure will be described with reference to FIGS. 12 to 14. FIG. 12 is a diagram illustrating a configuration of a main portion of a light source device according to the fourth embodiment of the disclosure. An endoscope system according to the present fourth embodiment has the same configuration as that of the first embodiment described above except for the configuration of emission units. Hereinafter, portions different from the above-described first embodiment will be described. Hereinafter, the configuration of the main portion of the first emission unit will be described, but the second emission unit and the third emission unit can be similarly configured.

The first emission unit according to the present fourth embodiment includes cylindrical lenses 350G in addition to the configuration of the first emission unit 310G described above. Note that the orientations of the H direction and the V direction in each light source have, for example, the same relationship as in the third embodiment. The cylindrical lenses 350G are provided between the first lenses 313G and the condenser lens 314G. The cylindrical lenses 350G convert an elliptical beam into a perfect circular beam. The cylindrical lenses 350G convert light having an elliptical light distribution into light having a perfect circular light distribution.

Figure 13:
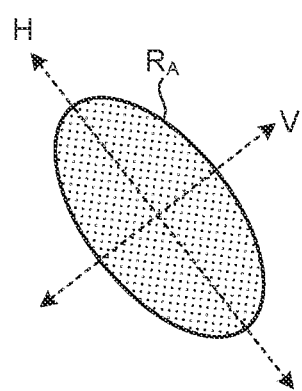
FIG. 13 is a diagram illustrating a beam forming region of a light source in the light source device according to the fourth embodiment of the disclosure.
Figure 14:
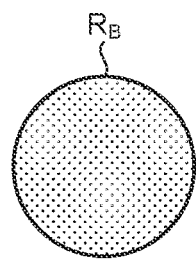
FIG. 14 is a diagram illustrating the beam forming region of the light source in the light source device according to the fourth embodiment of the disclosure.

FIGS. 13 and 14 are diagrams illustrating a beam forming region of the light source in the light source device according to the fourth embodiment of the disclosure. FIG. 13 illustrates a light distribution Ra before being incident on the cylindrical lenses 350G (a plane $P_A$ in FIG. 12). FIG. 14 illustrates a light distribution $R_B$ after passing through the cylindrical lenses 350G (a plane $P_B$ in FIG. 12). In a case where light having an elliptical light distribution (see FIG. 13) is emitted from a light source including a semiconductor laser, when the light enters the cylindrical lenses 350G, the light is converted into light having a perfect circular light distribution (see FIG. 14). Note that the H direction and the V direction illustrated in FIG. 13 correspond to the major axis direction and the minor axis direction of the ellipse in the light distribution described in the third embodiment.

According to the present fourth embodiment, in addition to the effects of the first embodiment described above, by arranging the cylindrical lenses 350G between the first lenses 313G and the condenser lens 314G, it is possible to reduce the difference between the irradiation ranges in the H direction and the V direction described above and to suppress unevenness in light distribution.

Fifth Embodiment

Figure 15:
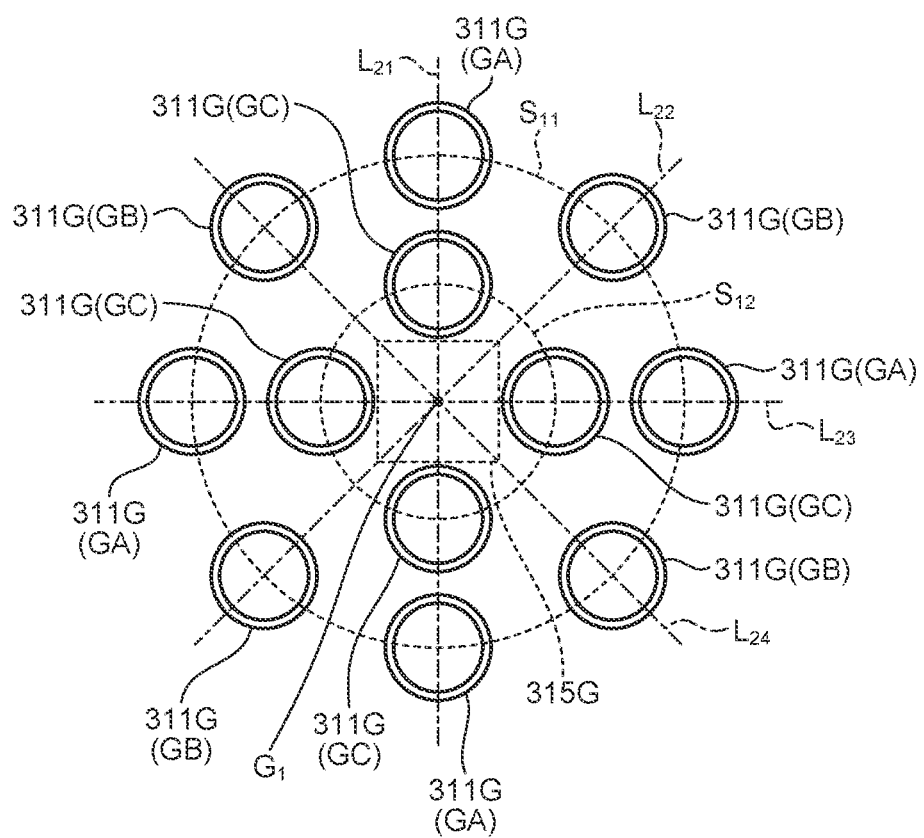
FIG. 15 is a diagram illustrating an arrangement of light sources in a light source device included in an endoscope system according to a fifth embodiment of the disclosure.

Next, a fifth embodiment of the disclosure will be described with reference to FIGS. 15 to 19. FIG. 15 is a diagram illustrating arrangement of light sources in a light source device included in an endoscope system according to the fifth embodiment of the disclosure. An endoscope system according to the present fifth embodiment has the same configuration as that of the first embodiment described above except for the configuration of emission units. Hereinafter, portions different from the above-described first embodiment will be described. Hereinafter, the configuration of the main portion of the first emission unit will be described, but the second emission unit and the third emission unit can be similarly configured.

The first emission unit according to the present fifth embodiment is different from the above-described first emission unit 310G in the number and arrangement of the first light sources 311G. In the present fifth embodiment, twelve first light sources 311G are provided. Each of the first light sources 311G is arranged on one of two different circles. Specifically, the first light sources 311G are arranged on one of two circles $S_{11}$ and $S_{12}$ having different diameters from each other with the center of gravity $G_1$ of the rod 315G as a center in a plan view as viewed in the central axis direction of the rod 315G. Here, the diameter of the circle Su is larger than the diameter of the circle $S_{12}$, and is equal to or less than an effective diameter of the condenser lens 314G. Further, any one of straight lines $L_{21}$ to $L_{24}$ passing through the center of gravity $G_1$ of the rod 315G passes through each of the first light sources 311G. The straight lines $L_{21}$ and $L_{23}$ pass through the center (center of gravity) of the first light sources 311G and are orthogonal to side surfaces, respectively, which intersect the straight line among side surfaces of the rod 315G. Furthermore, the straight lines $L_{22}$ and $L_{24}$ pass through the center (center of gravity) of the first light sources 311G and pass through two vertices facing across the center of gravity $G_1$ from one another among four vertices of the rod 315G.

In the present fifth embodiment, each of the first light sources 311G is divided into the following three groups according to the arrangement with respect to the rod 31SG.

Group A (GA): composed of the first light sources 311G which are arranged on the circle Su and through which the straight lines $L_{21}$ and $L_{23}$ pass.

Group B (GB): composed of the first light sources 311G which are arranged on the circle $S_{11}$ and through which the straight lines $L_{22}$ and $L_{24}$ pass.

Group C (GC): composed of the first light sources 311G arranged on the circle $S_{12}$.

Since an incident angle and an incident position of light with respect to the rod 315G are different, a light distribution of each group is also different. For example, the group A corresponds to the light source arrangement of the first embodiment described above, and the traveling direction of the light incident on the rod 315G is perpendicular to the reflecting surface of the rod 315G. In the group B, the distance to the center of gravity $G_1$ of the rod 315G is the same as that in the group A, but the light incident on the rod 315G is reflected at the corner of the rod 315G. In the group C, the traveling direction of the light incident on the rod 315G is perpendicular to the reflecting surface of the rod 315G, but the distance to the center of gravity $G_1$ of the rod 315G is shorter than that in the group A.

Figure 16:
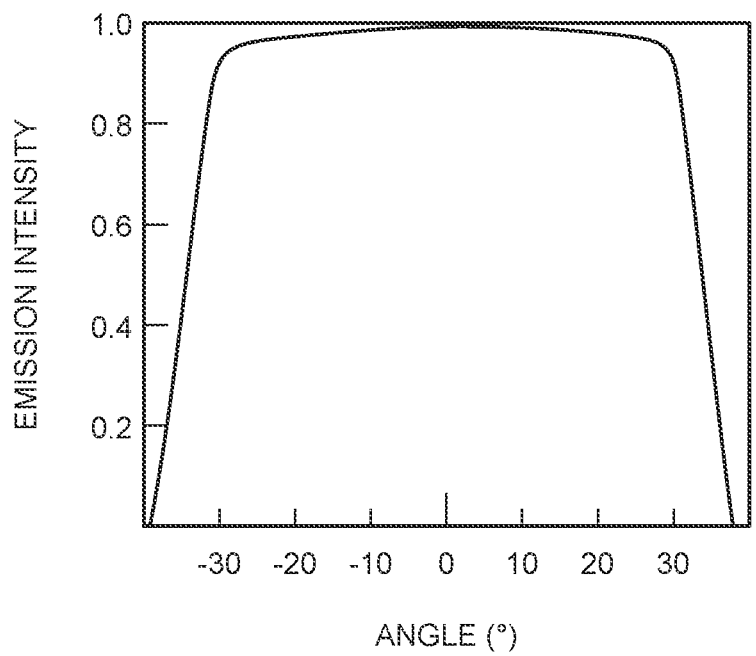
FIG. 16 is a diagram illustrating an emission intensity distribution of the light source in the light source device according to the fifth embodiment of the disclosure.
Figure 17:
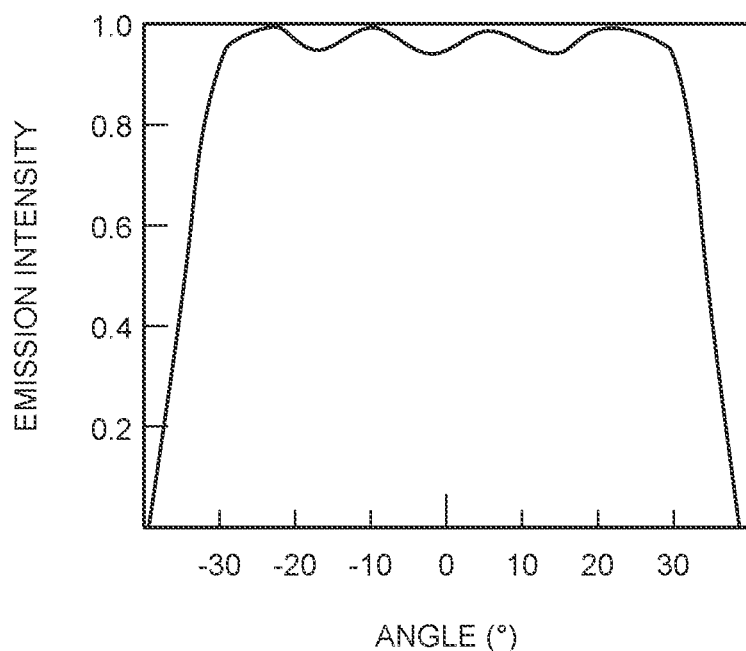
FIG. 17 is a diagram illustrating an emission intensity distribution of the light source in the light source device according to the fifth embodiment of the disclosure.
Figure 18:
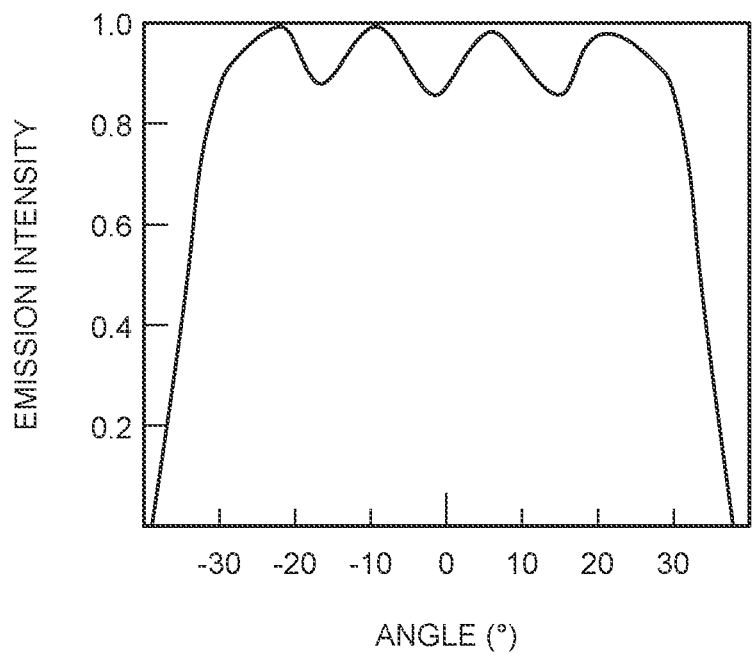
FIG. 18 is a diagram illustrating an emission intensity distribution of the light source in the light source device according to the fifth embodiment of the disclosure.

FIGS. 16 to 18 are diagrams illustrating an emission intensity distribution of the light source in the light source device according to the fifth embodiment of the disclosure. FIG. 16 illustrates the emission intensity distribution of the group A. FIG. 17 illustrates the emission intensity distribution of the group 8. FIG. 18 illustrates the emission intensity distribution of the group C. In FIGS. 16 to 18, the center of the light source is set to 0°, and the emission intensity of light in a direction inclined with respect to the optical axis passing through the central axis is illustrated. Note that FIGS. 16 to 18 illustrate values normalized with the maximum value of each emission intensity as 1.

Comparing FIGS. 16 to 18, the unevenness of the emission intensity of the group A is the smallest, and the unevenness of the emission intensity of the group C is the largest. In this example, the group C in which a distance to the rod 315G is short is a light source group having the largest unevenness.

Figure 19:
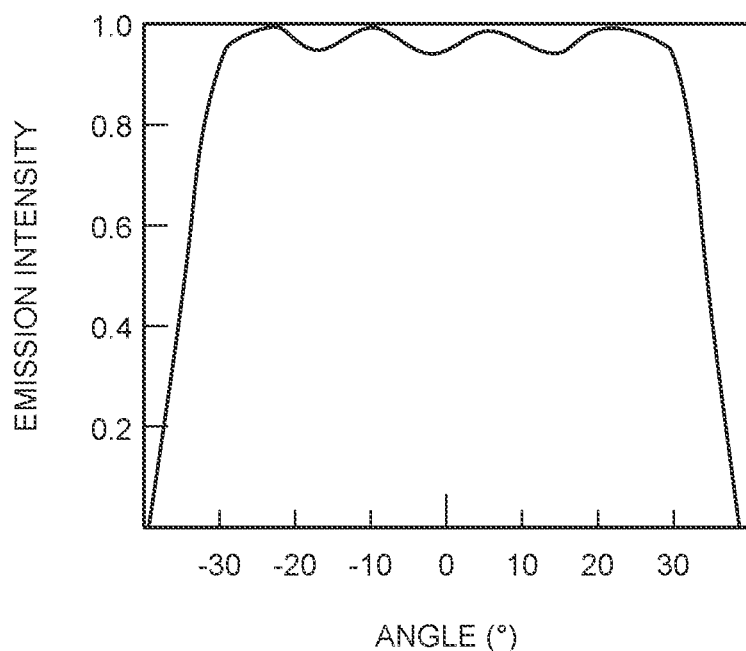
FIG. 19 is a diagram illustrating an emission intensity distribution after light mixing in the light source device according to the fifth embodiment of the disclosure.

When the light sources of the respective groups are simultaneously turned on, the respective lights are reflected in the rod 315G and mixed. FIG. 19 is a view illustrating an emission intensity distribution after light mixing in the light source device according to the fifth embodiment of the disclosure. In FIG. 19, the center of the light source is set to 0°, and the emission intensity of light in a direction inclined with respect to the optical axis passing through the central axis is illustrated. Note that FIG. 19 illustrates values normalized with the maximum value of each emission intensity as 1. By mixing the light of the group A to the group C by the rod 315G, the light in which the unevenness of the emission intensity is suppressed is generated. In particular, even in the case of including the group C in which the intensity unevenness is large, the unevenness is suppressed by mixing with the light of the group A or the group B.

In the present fifth embodiment, in addition to the effect of the first embodiment described above, even in a case where the number of light sources is increased, it is possible to generate light in which unevenness in intensity due to the arrangement with respect to the rod 315G is suppressed. According to the present fifth embodiment, it is possible to suppress unevenness while increasing a light amount.

In the present fifth embodiment, even when the light sources of the group C having the large unevenness of the intensity are used, the unevenness is suppressed by mixing with the light of the light sources of the group A having the small unevenness of the intensity in the rod 315G. Therefore, compared with a case where only the light sources of the group C are used, the length in the longitudinal direction of the rod 315G (the length necessary for suppressing the unevenness) can be suppressed from becoming long.

Sixth Embodiment

Figure 20:
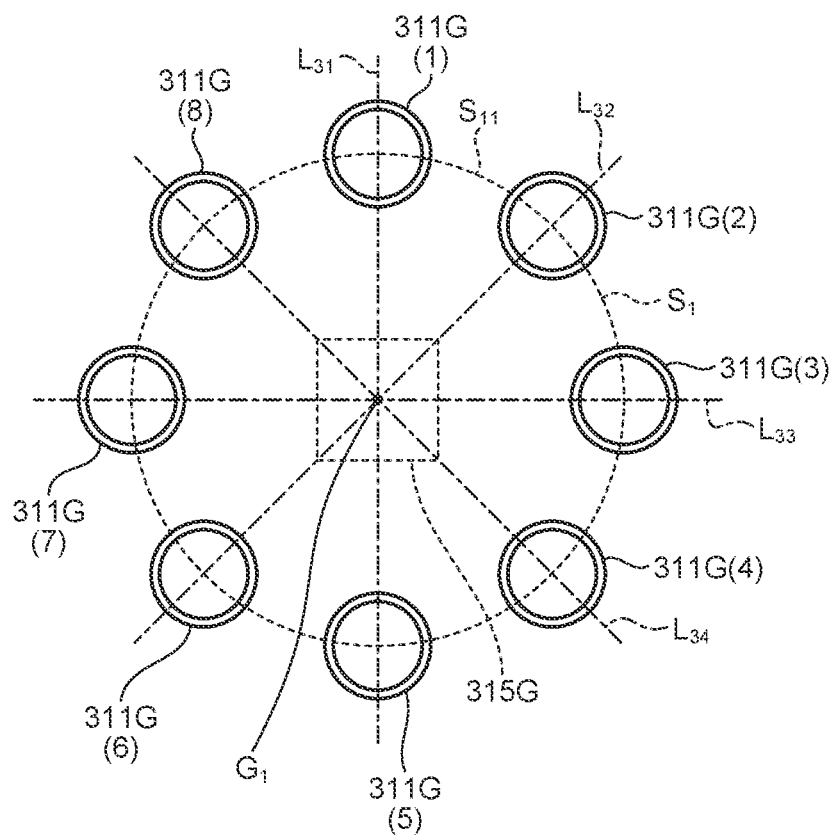
FIG. 20 is a diagram illustrating an arrangement of light sources in a light source device included in an endoscope system according to a sixth embodiment of the disclosure.
Figure 21:
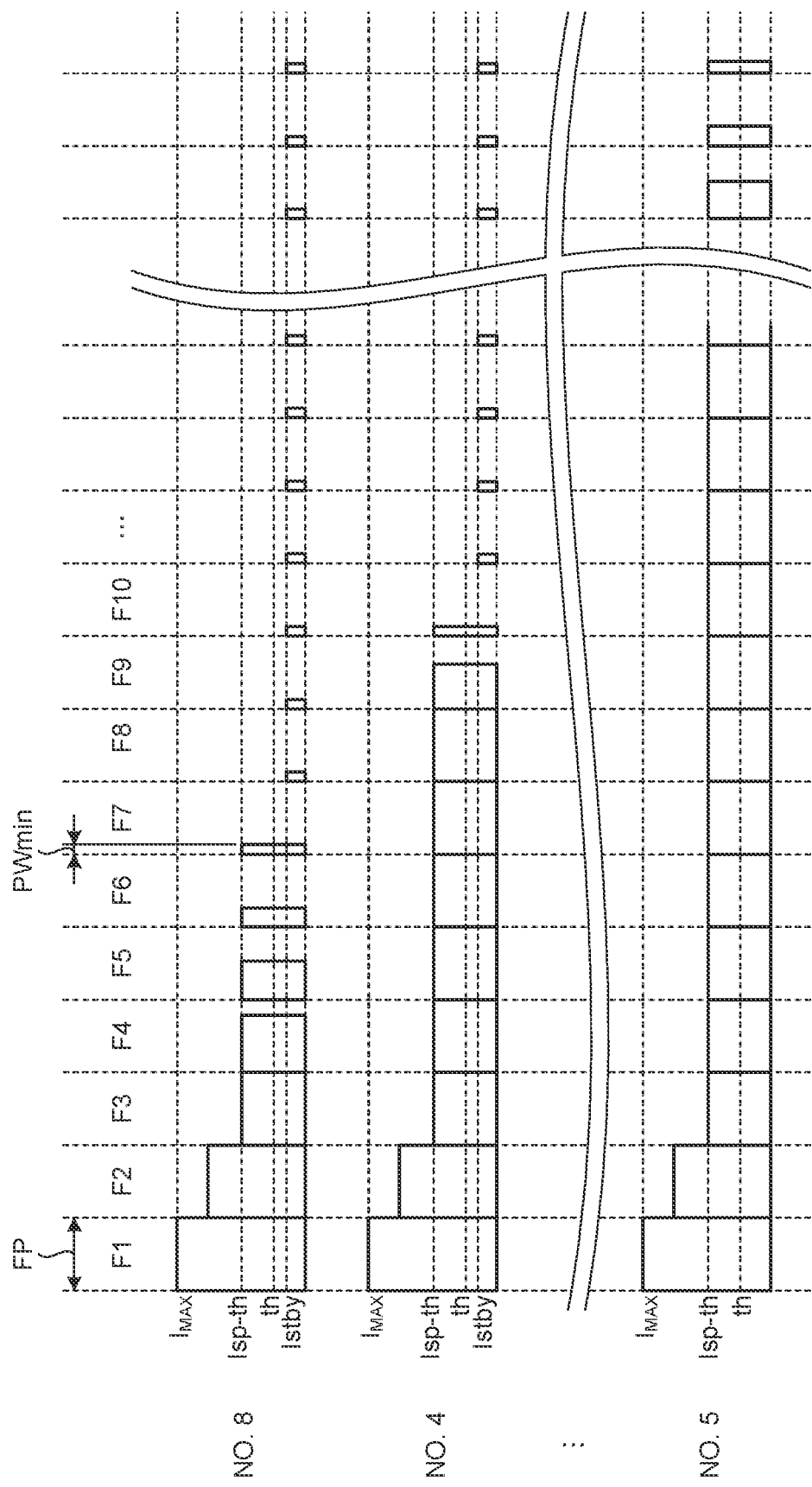
FIG. 21 is a diagram illustrating an example of an emission pattern of the light sources in the light source device included in the endoscope system according to the sixth embodiment of the disclosure.

Next, a sixth embodiment of the disclosure will be described with reference to FIGS. 20 and 21. FIG. 20 is a diagram illustrating an arrangement of light sources in a light source device included in an endoscope system according to the sixth embodiment of the disclosure. An endoscope system according to the present sixth embodiment has the same configuration as that of the first embodiment described above except for the configuration of emission units. Hereinafter, portions different from the above-described first embodiment will be described. Hereinafter, the configuration of the main portion of the first emission unit will be described, but the second emission unit and the third emission unit can be similarly configured.

The first emission unit according to the present sixth embodiment is different from the above-described first emission unit 310G in the number and arrangement of the first light sources 311G. In the present sixth embodiment, eight first light sources 311G are provided. Each of the first light sources 311G is arranged on a circle $S_1$ centered on the center of gravity $G_1$ of the cod 315G in a plan view as viewed in the central axis direction of the rod 315G. Further, any one of straight lines $L_{31}$ to $L_{34}$ passing through the center of gravity $G_1$ of the rod 315G passes through each of the first light sources 311G. The straight lines $L_{31}$ and $L_{33}$ pass through the center (center of gravity) of the first light sources 311G and are orthogonal to side surfaces, respectively which intersect the straight line among side surfaces of the rod 315G. Furthermore, the straight lines $L_{32}$ and $L_{34}$ pass through the center (center of gravity) of the first light sources 311G and pass through two vertices facing across the center of gravity $G_1$ from one another among four vertices of the rod 315G.

In the present sixth embodiment, each of the first light sources 311G is numbered according to a circumferential direction with respect to the rod 315G. Specifically, the number 1 is assigned to one of the first light sources 311G through which the straight line $L_{31}$ passes, and the numbers from the first light source 311G with the number 1 to the first light source 311G with the number 8 are assigned to each of the first light sources. In an example illustrated in FIG. 20, numbers are assigned clockwise (see the numerical values in parentheses in FIG. 20).

The first light sources 311G through which the straight lines $L_{31}$ and $L_{33}$ pass correspond to the light sources of the group A described above. On the other hand, the first light sources 311G through which the straight lines $L_{32}$ and $L_{34}$ pass correspond to the light sources of the group B described above. Therefore, the first light sources 311G through which the straight lines $L_{31}$ and $L_{33}$ pass have smaller unevenness in light intensity than the first light sources 311G through which the straight lines $L_{32}$ and $L_{34}$ pass (see FIGS. 16 and 17).

Emission control of the light sources according to the present sixth embodiment will be described with reference to FIG. 21. FIG. 21 is a diagram illustrating an example of an emission pattern of the light sources in the light source device included in the endoscope system according to the sixth embodiment of the disclosure. FIG. 21 illustrates an example in which an amount of emitted light is reduced over a plurality of frames after all the first light sources 311G are turned on in the first frame (F1).

In a turn-off order of the first light sources 311G, the first light sources 311G corresponding to the group B are turned off first, and then the first light sources 311G corresponding to the group A are turned off. For example, the light is turned off in the order of No. 8, No. 4, No. 2, No. 6, No. 7, No. 3, No. 1, and No. 5. In an example illustrated in FIG. 21, a light amount per frame is reduced by reducing a pulse height corresponding to the light amount or reducing a pulse width corresponding to the emission time for each frame. For example, from the second frame (F2) to the third frame, the pulse heights of all the light sources are reduced to a first threshold (Isp-th). Thereafter, the pulse width is sequentially reduced from the eighth light source, and after the pulse width reaches the minimum width (PWmin), the pulse width is reduced to a pulse height smaller than a second threshold (th) which is a lower limit value of light emission.

Here, the first threshold is a value set to uniformly lower the entire light amount when the light is turned off, and is set on the basis of a lower limit value of the light amount at which speckle hardly occurs. As the second threshold, a pulse height for not emitting light as a light source and waiting until next light emission is set. As the minimum width of the pulse width, a minimum controllable pulse width is set.

The information regarding the control of the light sources described above is stored in, for example, the illumination information storage unit 451.

In the present sixth embodiment, in addition to the effect of the first embodiment described above, when the light sources are turned off, the light sources are sequentially turned off from the light sources having large light distribution unevenness, so that it is possible to suppress the unevenness of the light intensity when the light amount decreases at the time of turning off.

Modification of Sixth Embodiment

Figure 22:
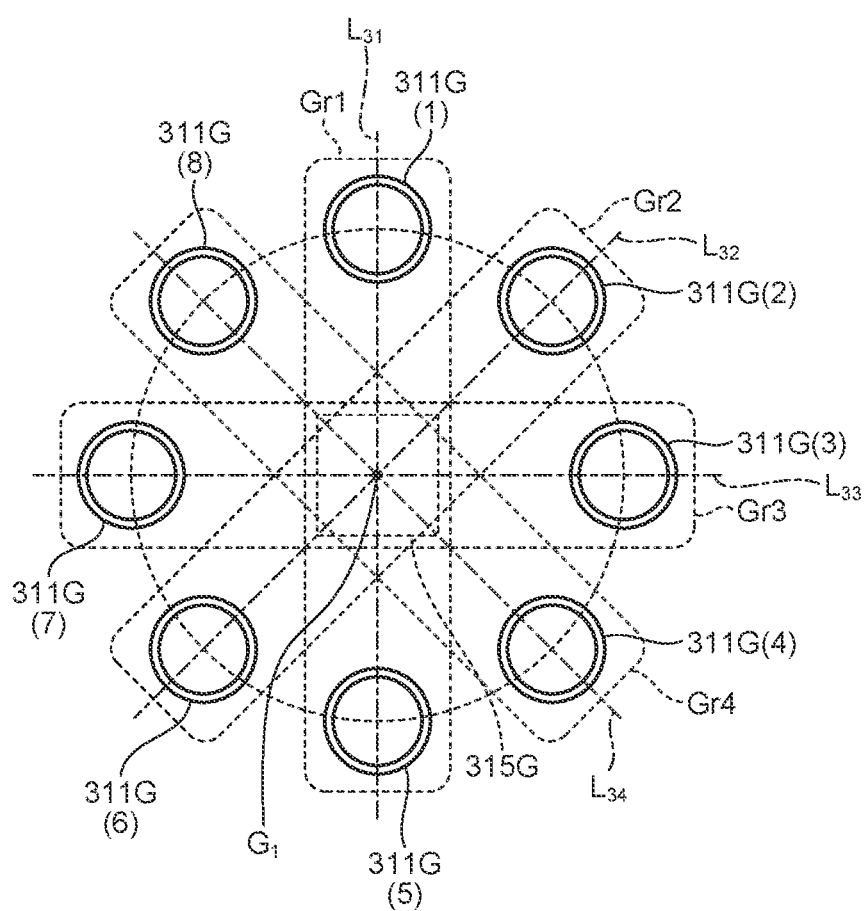
FIG. 22 is a diagram illustrating an arrangement of light sources in a light source device included in an endoscope system according to a modification of the sixth embodiment of the disclosure.
Figure 23:
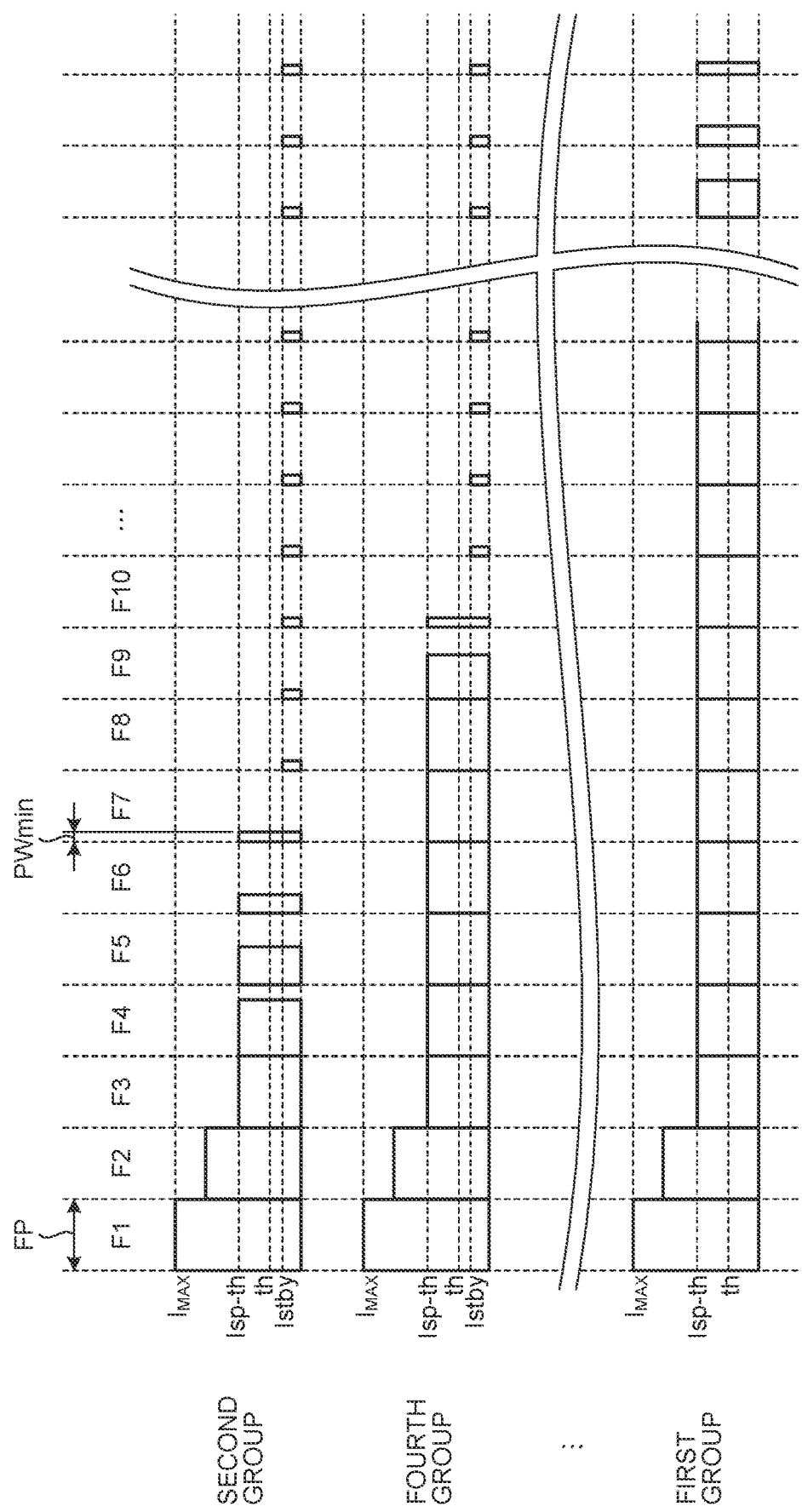
FIG. 23 is a diagram illustrating an example of an emission pattern of the light sources in the light source device included in the endoscope system according to the modification of the sixth embodiment of the disclosure.

Next, a modification of the sixth embodiment of the disclosure will be described with reference to FIGS. 22 and 23. FIG. 22 is a diagram illustrating an arrangement of light sources in a light: source device included in an endoscope system according to a modification of the sixth embodiment of the disclosure. An endoscope system according to the modification of the present sixth embodiment, has the same configuration as that of the sixth embodiment described above. Hereinafter, processing different from that of the sixth embodiment described above will be described.

In the present modification, light emission is controlled using light sources through which the same straight line passes as a set. Specifically, the first and fifth first light sources 311G through which a straight line $L_{31}$ passes are defined as a first, group (Gr1), the second and sixth first light sources 311G through which a straight line $L_{32}$ passes are defined as a second group (Gr2), the third and seventh first light sources 311G through which a straight line $L_{33}$ passes are defined as a third group (Gr3), and the fourth and eighth first light sources 311G through which a straight line $L_{34}$ passes are defined as a fourth group (Gr4).

Emission control of the light sources according to the present modification will be described with reference to FIG. 23. FIG. 23 is a diagram illustrating an example of an emission pattern of the light sources in the light source device included in the endoscope system according to the modification of the sixth embodiment of the disclosure. Similarly to FIG. 21, FIG. 23 illustrates an example in which the amount of emitted light is reduced over a plurality of frames after all the first light sources 311G are turned on in the first frame (F1).

In a turn-off order of the first light sources 311G, the light sources belonging to the second group and the fourth group are turned off, and then the light sources belonging to the first group and the third group are turned off. For example, the light is turned off in the order of the second group, the fourth group, the third group, and the first group. For example, from the second frame (F2) to the third frame, the pulse heights of all the light sources are reduced to a first threshold (Isp-th). Thereafter, the pulse width is sequentially reduced from the light sources of the second group, and after the pulse width reaches the minimum width (PWmin), the pulse width is reduced to a pulse height smaller than a second threshold (th) which is a lower limit value of light emission.

In the present modification, in addition to the effect of the first embodiment described above, when the light sources are turned off, the light sources of the group having large light distribution unevenness is sequentially turned off, so that it is possible to suppress the unevenness of light distribution when the light amount decreases at the time of turning off.

Seventh Embodiment

Figure 24:
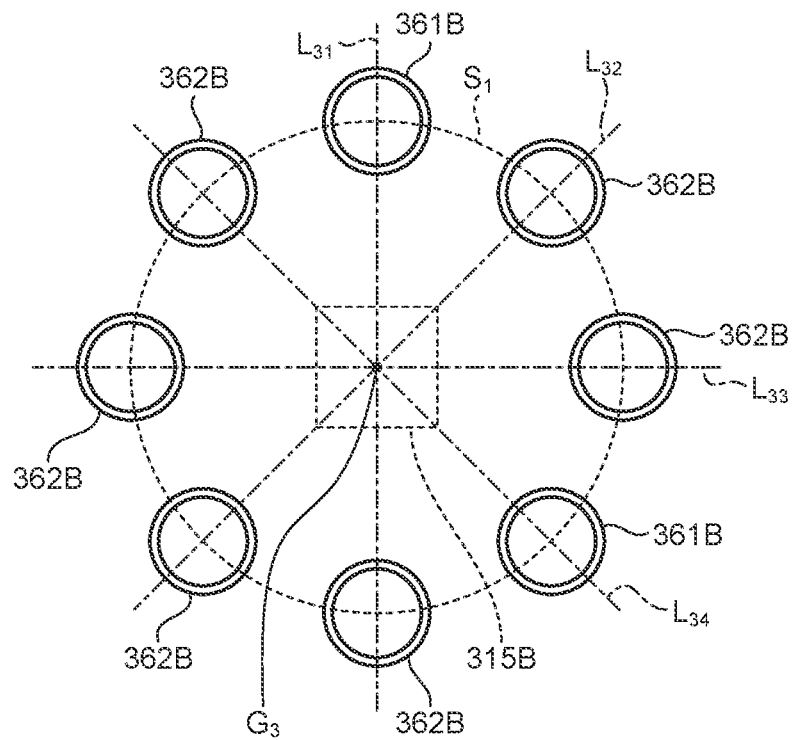
FIG. 24 is a diagram illustrating an arrangement of light sources in a light source device included in an endoscope system according to a seventh embodiment of the disclosure.

Next, a seventh embodiment of the disclosure will be described with reference to FIG. 24. FIG. 24 is a diagram illustrating an arrangement of light sources in a light source device included in an endoscope system according to the seventh embodiment of the disclosure. An endoscope system according to the seventh embodiment has the same configuration as that of the first embodiment described above except for the configuration of emission units. Hereinafter, portions different from the above-described first embodiment will be described. Hereinafter, the configuration of a main portion of a second emission unit will be described as an example.

The second light emission unit according to the present seventh embodiment is different from the above-described second emission unit 310B in the number and arrangement of the second light sources. In the present seventh embodiment, eight second light sources are provided as in the sixth embodiment. Each of the second light sources is arranged on a circle $S_1$ centered on the center of gravity $G_3$ of the rod 315B in a plan view as viewed in the central axis direction of the rod 315B. Further, any one of straight lines $L_{31}$ to $L_{34}$ passing through the center of gravity $G_3$ of the rod 315G passes through each of the second light sources.

In the present seventh embodiment, as the second light sources, a plurality of types of light sources having wavelengths different from each other in a blue wavelength band are used. Specifically, second light sources 361B that emit light in a wavelength band of 470 nm or more, and second light sources 362B that emit light of 445 nm are used. In an example illustrated in FIG. 24, the second light sources 361B are arranged at a position passing through one of the straight lines $L_{31}$ and a position passing through one of the straight lines $L_{34}$. The second light sources 362B are arranged at other positions.

In addition, a light source that emits light of 455 nm can be provided as a light source that emits blue light. Furthermore, a light source that emits light of 520 nm or 532 nm can also be provided in an emission unit that emits green light.

In the present seventh embodiment, when a plurality of light sources having the same wavelength are arranged, at least one of the plurality of light sources is arranged on a straight line (here, the straight lines $L_{32}$ and $L_{34}$) passing through a corner portion of the rod 315B. In an example illustrated in FIG. 24, in the case of using a plurality of types of light sources that emit light of different wavelengths, each light source is arranged at a position where unevenness of light intensity is uniformized.

In addition to the effects of the first embodiment described above, the present seventh embodiment includes a plurality of types of light sources having different wavelengths within a wavelength band of the same color, so that color reproducibility can be improved. Furthermore, by illuminating an object with light in a specific wavelength band, visibility of a specific observation object can be improved.

Here, in the seventh embodiment, a light source having a wavelength corresponding to special light observation can be arranged. For example, in auto fluorescence imaging (AFI) observation, excitation light of 390 nm to 470 nm is emitted to detect autofluorescence of 490 nm to 630 nm. In the AFI observation, in order to acquire fluorescence, a filter that cuts light in a wavelength band of excitation light is provided in an imaging element, at the time of the AFI observation. Therefore, the second emission unit is provided with, for example, a light source that emits light of 445 nm and a light source that emits light in a wavelength band of 470 nm or more. When the AFI observation is performed, a light source of 445 nm is emitted, and when normal white light observation is performed, a light source of 470 nm or more is emitted.

In ICG-PDD observation, indocyanine green (ICG) is intravenously injected, and ICG is excited by light of 780 nm to 800 nm to observe fluorescence around 830 nm. In the ICG-PDD observation, a blood vessel image of a deep part of a living body can be obtained by fluorescence of 830 nm. In order to support the ICG-PDD observation, a light source that emits light of 780 nm to 800 nm is arranged in an emission unit (for example, the third emission unit 310R) that emits red light.

In confocal endoscopic observation, fluorescein that is excited by light of 494 nm and emits fluorescence having a peak at 521 nm is used. In order to support the confocal endoscopic observation, a light source that emits light of 494 nm is arranged in an emission unit that emits blue light (for example, the second emission unit 310B) or an emission unit that emits green light (for example, the first emission unit 310G).

In near-infrared photoimmunotherapy, IRDye that emits fluorescence excited at 690 nm and having a peak at 830 nm is used. In order to cope with the near-infrared photoimmunotherapy, a light source that emits light of 690 nm is arranged in an emission unit (for example, the third emission unit 310R) that emits red light.

In the seventh embodiment, by changing some light sources, it is possible to arrange light sources corresponding to special light without changing the basic design.

In addition, it is possible to configure such that some light source arrangement positions are emptied, and a user attaches a light source that emits light having a wavelength corresponding to observation to be performed.

Eighth Embodiment

Figure 25:
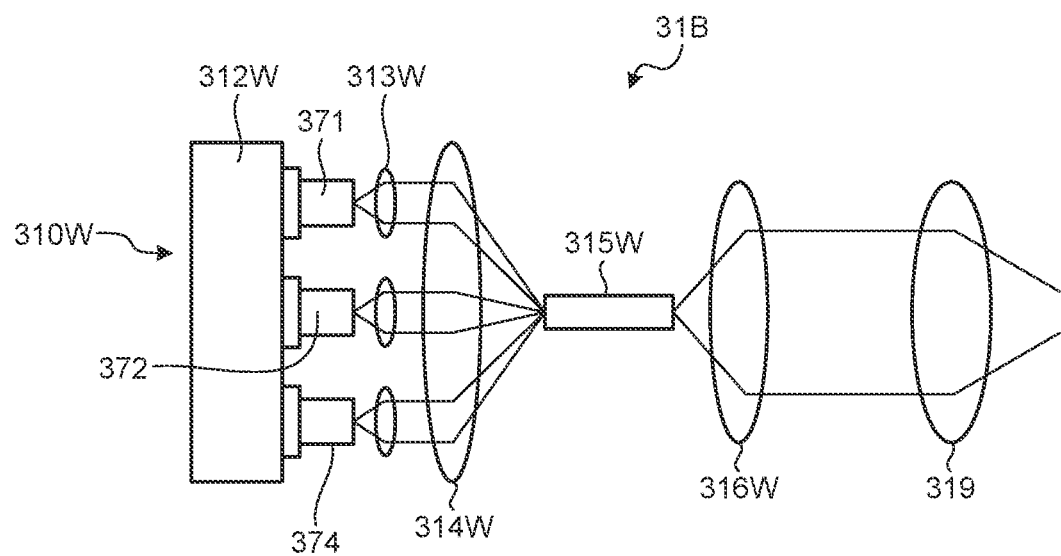
FIG. 25 is a diagram illustrating a configuration of a main portion of a light source device included in an endoscope system according to an eighth embodiment of the disclosure.
Figure 26:
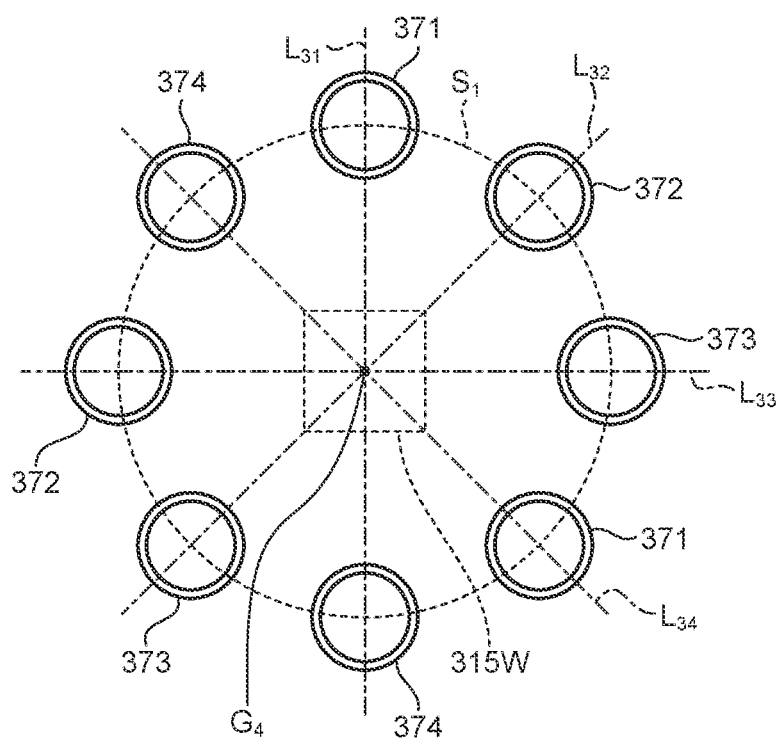
FIG. 26 is a diagram illustrating an arrangement of light sources in the light source device included in the endoscope system according to the eighth embodiment of the disclosure.

Next, an eighth embodiment of the disclosure will be described with reference to FIGS. 25 and 26. FIG. 25 is a diagram illustrating a configuration of a main portion of a light source device included in an endoscope system according to the eighth embodiment of the disclosure. FIG. 26 is a diagram illustrating an arrangement of light sources in the light source device included in the endoscope system according to the eighth embodiment of the disclosure. An endoscope system according to the present eighth embodiment has the same configuration except that the configuration of a light source unit in the light source device 3 of the endoscope system 1 described above is changed. Hereinafter, a configuration of a main portion (light source unit 31B) of the light source device different from the above-described first embodiment will be described.

The light source unit 313 according to the present eighth embodiment includes an emission unit 310W provided with a plurality of light sources. Specifically, the emission unit 310W includes two first light sources 371 that emit green illumination light, two second light sources 372 that emit blue illumination light, two third light sources 373 that emit red illumination light, and two fourth light sources 374 that emit light in a wavelength band of 380 to 450 nm (violet illumination light).

Furthermore, in addition to the light sources described above, the emission unit 310W includes a holder 312W in which each light source is arranged, first lenses 313W that guide the illumination light emitted from each light source, a condenser lens 314W that condenses the illumination light passing through the first lenses 313W, a rod 315W into which the light condensed by the condenser lens 314W is introduced and that emits light having a uniform illuminance distribution, and a collimator lens 316W that converts the light emitted from the rod into parallel light.

The rod 315W extends in a prismatic shape, and has a rectangular outer edge (cross section) in a direction orthogonal to a longitudinal direction. The central axis extending in the longitudinal direction of the rod 315W coincides with the optical axis of the optical system including the first lenses 313W, the condenser lens 314W, the rod 315W, and the collimator lens 316W.

The light source unit 31B includes the second lens 319 described above. The second lens 319 condenses the light from the collimator lens 316W and emits the light to the light guide 241.

The first light source 371 to the fourth light source 374 are arranged on a circle $S_1$ centered on the center of gravity $G_4$ of the rod 315W in a plan view as viewed in the central axis direction of the rod 315W. Further, any one of straight lines $L_{31}$ to $L_{34}$ passing through the center of gravity $G_4$ of the rod 315W passes through each light source (first light source 371, second light source 372, third light source 373, and fourth light source 374). Here, the light sources in the same wavelength band are arranged on one of the straight line $L_{31}$ and the straight line $L_{33}$ and one of the straight line $L_{32}$ and the straight line $L_{34}$, respectively. Therefore, one of the first light source 371 to the fourth light source 374 is arranged at a position through which the straight lines $L_{31}$ and $L_{33}$ pass, and the other of the first light source 371 to the fourth light source 374 is arranged at a position through which the straight lines $L_{32}$ and $L_{34}$ pass.

The light emitted from the light sources enters the condenser lens 314W through the first lenses 313W. The light incident on the condenser lens 314W is bent and incident on the rod 315W. At this time, a traveling direction (optical axis) of the light incident on the rod 315W is inclined with respect to the central axis of the rod 315W. The traveling direction of the light incident on the rod 315W is perpendicular to the light reflecting surface of the rod 315W.

The light incident on the rod 315W travels toward an end portion of the rod 31SW on a side opposite to incident side while being reflected. Specifically, when the light is incident on the rod 315W and is repeatedly reflected, the light of each wavelength band of each light source is mixed, and the white light in which the positional unevenness is eliminated is generated.

In the eighth embodiment described above, similarly to the first embodiment, a plurality of light sources are arranged at positions that are provided around the rod 315W and allow light to enter in a direction perpendicular to a reflecting surface in the rod (for example, a reflecting surface in the rod 315W) in a plan view as viewed in the central axis direction of the rod 315W. According to the present eighth embodiment, since the light emitted from each light source is incident to incline with respect to the central axis of the rod and is mixed by repeating reflection in the rod a plurality of times, it is possible to uniformly mix the light from the plurality of light sources and emit the light with suppressed illuminance unevenness. As a result, the illuminance at the center of the effective irradiation range and the illuminance around the center are more reliably uniformized, and an object can be irradiated with light in which the illuminance unevenness is suppressed.

In addition, in the present eighth embodiment, since the light sources of the respective colors are arranged in one holder 312W to generate the white light, the size can be reduced as compared with the light source unit 31.

In the present eighth embodiment, the light sources may not be arranged at the positions where the straight lines $L_{32}$ and $L_{34}$ pass, that is, the light sources may be arranged only at the positions where the straight lines $L_{31}$ and $L_{33}$ pass.

Ninth Embodiment

Figure 27:
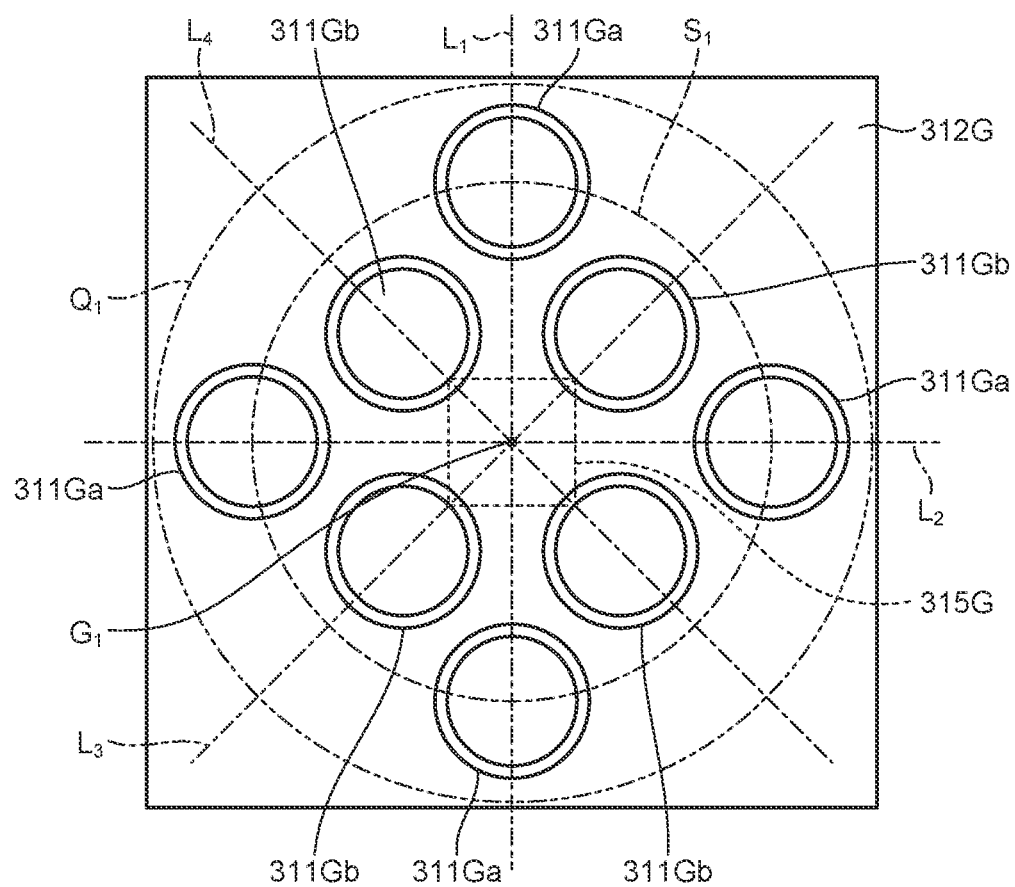
FIG. 27 is a diagram illustrating a configuration of a main portion of a light source device according to a ninth embodiment of the disclosure.

Next, a ninth embodiment of the disclosure will be described with reference to FIG. 27. FIG. 27 is a diagram illustrating a configuration of a main portion of a light source device included in an endoscope system according to the ninth embodiment of the disclosure. An endoscope system according to the present ninth embodiment has the same configuration as that of the first embodiment described above except for the configuration of emission units. Hereinafter, portions different from the above-described first embodiment will be described. Hereinafter, the configuration of the main portion of the first emission unit will be described, but the second emission unit and the third emission unit can be similarly configured.

The first emission unit according to the present ninth embodiment includes fine adjustment light sources 311Ga and large light amount light sources 311Gb instead of the second light sources 311B with respect to the first emission unit 310G described above. Since the other configurations are the same, the description thereof will be omitted.

The fine adjustment light sources 311Ga are arranged at the same positions as the first light sources 311G of the first embodiment. That is, the fine adjustment light sources 311Ga are provided on straight lines $L_1$ and $L_2$ orthogonal to side surfaces, respectively, which intersect the straight line among side surfaces of the rod 315G in a plan view as viewed in the central axis direction of the rod 315G.

In addition, the large light amount light sources 311Gb are provided on the straight lines $L_3$ and $L_4$ passing through two vertices facing across the center of gravity $G_1$ from one another among four vertices of the rod 315G. In the present ninth embodiment, the straight lines $L_2$ and $L_4$ coincide with diagonal lines on a light source arrangement surface of the holder 312G.

Here, a two-dot chain line $Q_1$ illustrated in FIG. 27 indicates the maximum diameter of an effective diameter of the condenser lens 314G.

The light incident on the rod 315G travels toward an end portion of the rod 315G on a side opposite to incident side while being reflected, similarly to the first embodiment. Specifically, the fine adjustment light and the large amount, of light are mixed by being incident on the rod 315G and repeatedly reflected, and the white light in which the positional unevenness is eliminated is generated.

In the ninth embodiment described above, similarly to the first embodiment, a plurality of light sources are arranged at positions that are provided around the rod and allow light to enter in a direction perpendicular to the reflecting surface in the rod (for example, the reflecting surface in the rod 315G) in a plan view as viewed in the central axis direction of the rod. According to the present ninth embodiment, since the light emitted from each light source is incident to incline with respect to the central axis of the rod and is mixed by repeating reflection in the rod a plurality of times, it is possible to uniformly mix the light from the plurality of light sources and emit the light with suppressed illuminance unevenness. As a result, the illuminance at the center of the effective irradiation range and the illuminance around the center are more reliably uniformized, and an object can be irradiated with light in which the illuminance unevenness is suppressed.

Furthermore, in the present ninth embodiment, the fine adjustment light sources are arranged at positions farther than the large light amount light sources with respect to the rod, and the effect of reducing unevenness is increased.

First Modification of Ninth Embodiment

Figure 28:
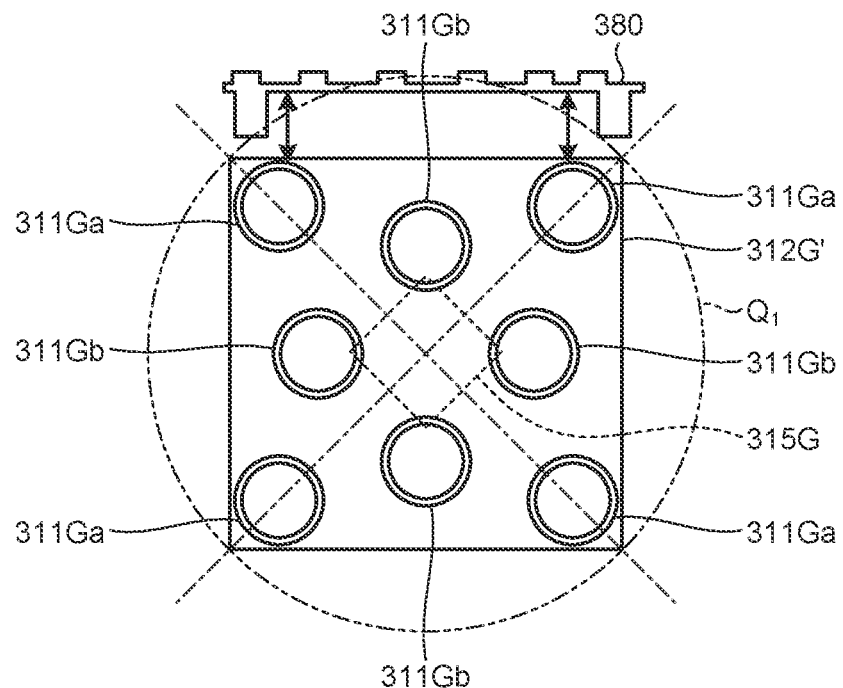
FIG. 28 is a diagram illustrating a configuration of a main portion of a light source device according to a first modification of the ninth embodiment of the disclosure.

Next, a first modification of the ninth embodiment of the disclosure will be described with reference to FIG. 28. FIG. 28 is a view illustrating a configuration of a main portion of a light source device according to the first modification of the ninth embodiment of the disclosure. An endoscope system according to the first modification of the ninth embodiment has the same configuration as that of the ninth embodiment described above except for an arrangement of the holder 312G with respect to the rod 315G. Hereinafter, portions different from the ninth embodiment described above will be described.

The first emission unit according to the first modification has a configuration in which the holder 312G is rotated by 45° with respect to the arrangement of the light sources and the rod 315G (in FIG. 28, the light sources and the rod 315G are rotated by 45°). The holder 312B after rotation is referred to as a holder 312G'. In the holder 312G', the fine adjustment light sources 311Ga are arranged at corner portions on the light source arrangement surface. Therefore, the holder 312G' can be made smaller than the holder 312G according to the ninth embodiment. For example, the holder 312G' can be sized to be inscribed in the two-dot chain line $Q_1$ indicating an outer edge of the condenser lens 314G.

In addition, the holder 312G' is provided with a substrate 380 connected to each light source. The substrate 380 is connected to all the light sources (the fine adjustment light sources 311Ga and the large light amount light sources 311Gb) by one substrate. At this time, the substrate 380 and a light source close to the substrate 380 (here, two fine adjustment light sources 311Ga) are connected at a shorter distance than the arrangement of the ninth embodiment. Thus, for example, the length of the wiring connecting the members can be minimized in design.

In the first, modification described above, similarly to the first embodiment, a plurality of light sources are arranged at positions that are provided around the rod and allow light to enter in a direction perpendicular to the reflecting surface in the rod (for example, the reflecting surface in the rod 315G) in a plan view as viewed in the central axis direction of the rod. According to the first modification, since the light emitted from each light source is incident to incline with respect to the central axis of the rod and is mixed by repeating reflection in the rod a plurality of times, it is possible to uniformly mix the light from the plurality of light sources and emit the light with suppressed illuminance unevenness. As a result, it is possible to irradiate an object with light in which the illuminance at the center of the effective irradiation range and the illuminance around the center are made uniform more reliably.

In addition, in the present first modification, since a part of the fine adjustment light sources (fine adjustment light sources 311Ga) is connected to the substrate (substrate 380) at the shortest distance, the wiring length between the substrate and the light sources is shortened, pulse rounding is suppressed, and the light sources can be controlled with high accuracy.

Second Modification of Ninth Embodiment

Figure 29:
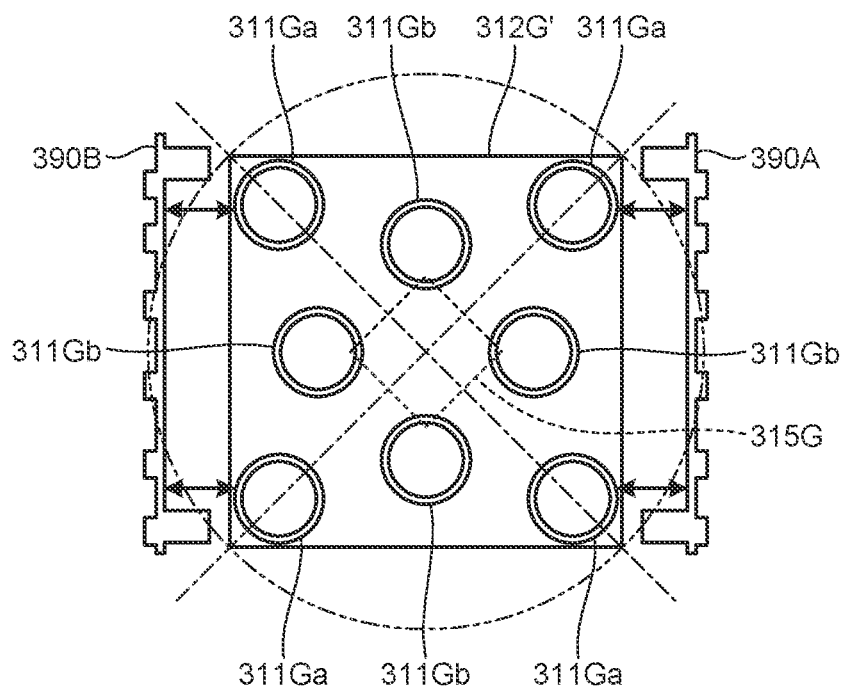
FIG. 29 is a diagram illustrating a configuration of a main portion of a light source device according to a second modification of the ninth embodiment of the disclosure.

Next, a second modification of the ninth embodiment of the disclosure will be described with reference to FIG. 29. FIG. 29 is a view illustrating a configuration of a main portion of a light source device according to the second modification of the ninth embodiment of the disclosure. An endoscope system according to the second modification of the ninth embodiment has the same configuration as that of the ninth embodiment described above except for an arrangement of the holder 312G with respect to the rod 315G. Hereinafter, portions different from the ninth embodiment described above will be described.

Similarly to the first modification, the first emission unit according to the second modification has a configuration in which the holder 312G is rotated by 45° with respect to the arrangement of the light sources and the rod 315G (in FIG. 29, the light sources and the rod 315G are rotated by 45°). The holder 312G after rotation is referred to as a holder 312G'. In the holder 312G', the fine adjustment light sources 311Ga are arranged at corner portions on the light source arrangement surface.

In addition, the holder 312G' is provided with two substrates (substrate 390A, 390B) connected to the respective light sources. The substrates 390A and 390B are provided on side surfaces facing across the light source arrangement surface from one another. Each light source (the fine adjustment light sources 311Ga and the large light amount light sources 311Gb) is connected to one of the substrates 390A and 390B. At this time, the substrate 390A is connected to a light source close to the substrate 390A (here, two fine adjustment light sources 311Ga on the substrate 390A side) at a shorter distance than the arrangement of the ninth embodiment. In addition, the substrate 390B is connected to a light source close to the substrate 390B (here, two fine adjustment light sources 311Ga on the substrate 390B side) at a shorter distance than the arrangement of the ninth embodiment.

In the second modification described above, similarly to the first embodiment, a plurality of light sources are arranged at positions that are provided around the rod and allow light to enter in a direction perpendicular to the reflecting surface in the rod (for example, the reflecting surface in the rod 315G) in a plan view as viewed in the central axis direction of the rod. According to the present second modification, since the light emitted from each light source is incident to incline with respect to the central axis of the rod and is mixed by repeating reflection in the rod a plurality of times, it is possible to uniformly mix the light from the plurality of light sources and emit the light with suppressed unevenness in illuminance. As a result, it is possible to irradiate an object with light in which the illuminance at the center of the effective irradiation range and the illuminance around the center are made uniform more reliably.

In the present second modification, in particular, each fine adjustment light source (fine adjustment light sources 311Ga) is connected to one of the two substrates (substrate 390A, 390B) at the shortest distance, so that the wiring length between each substrate and the light sources is shortened, pulse rounding is suppressed, and the light sources can be controlled with high accuracy.

Although the embodiments for carrying out the disclosure have been described so far, the disclosure should not be limited only by the above-described embodiments. The disclosure may include various embodiments and the like that are not described herein.

Furthermore, in the above-described first to ninth embodiments, it has been described that the light source device 3 is configured separately from the endoscope 2, but for example, a configuration in which the light source device is provided in the endoscope 2, such as providing a semiconductor laser at the distal end of the endoscope 2, may be adopted. Further, the function of the processing device 4 may be imparted to the endoscope 2.

In the present first to seventh and ninth embodiments, the configuration in which the light source unit includes the first emission unit that emits the green illumination light, the second emission unit that emits the blue illumination light, and the third emission unit that emits the red illumination light has been described as an example, but the light source unit may include four or more emission units. For example, in addition to the first to third emission units described above, a fourth emission unit that emits light in a wavelength band of 380 to 450 nm (violet illumination light) may be further included. The fourth emission unit is provided, for example, on the side (light guide side) opposite to the first emission unit of the second emission unit, and is further provided with a dichroic mirror that bends the light emitted from the fourth emission unit.

Furthermore, in the above-described first to ninth embodiments, the light source device 3 has been described as being separate from the processing device 4, but the light source device 3 and the processing device 4 may be integrated, and for example, the light source unit 31, the illumination control unit 32, and the light source driver 33 may be provided inside the processing device 4.

In addition, in the above-described first to ninth embodiments, the light source device 3 may include a white semiconductor laser and a rotary filter having three transmission filters that transmit each of a red wavelength band, a green wavelength band, and a blue wavelength band on an optical path of illumination light, and may emit illumination light including each of red, green, and blue wavelength bands by rotating the rotary filter.

Furthermore, in the above-described first to ninth embodiments described above, the endoscope system according to the disclosure has been described as the endoscope system 1 using the flexible endoscope 2 in which the observation target is a living tissue or the like in the subject. However, the disclosure can also be applied to an endoscope system using a rigid endoscope, an industrial endoscope for observing characteristics of a material, an endoscope using an eyepiece of an optical endoscope such as a capsule endoscope, a fiber scope, or an optical tube to which a camera head is connected.

Figure 30:
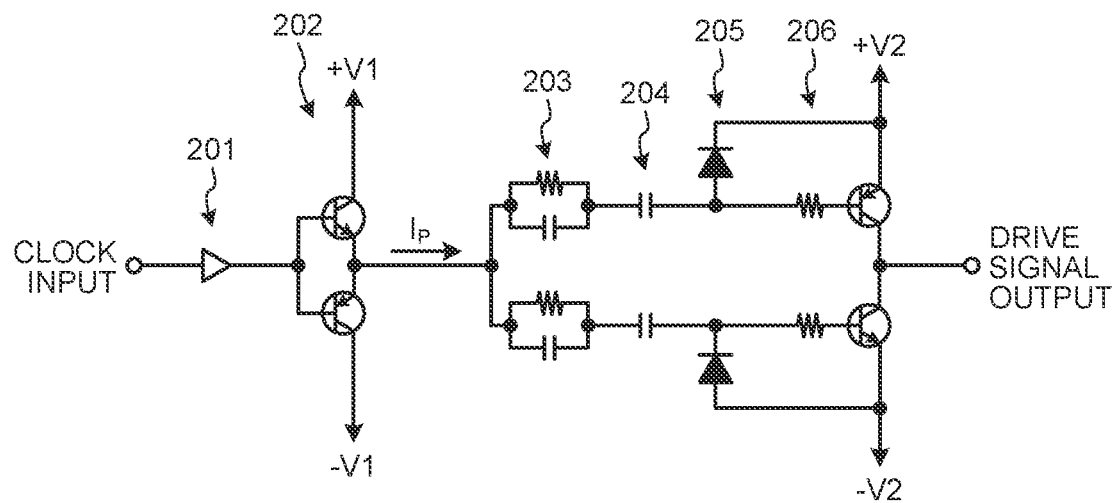
FIG. 30 is a diagram illustrating a circuit configuration for outputting a drive signal to an imaging element in a processing device, and is a diagram illustrating a conventional configuration.
Figure 31:
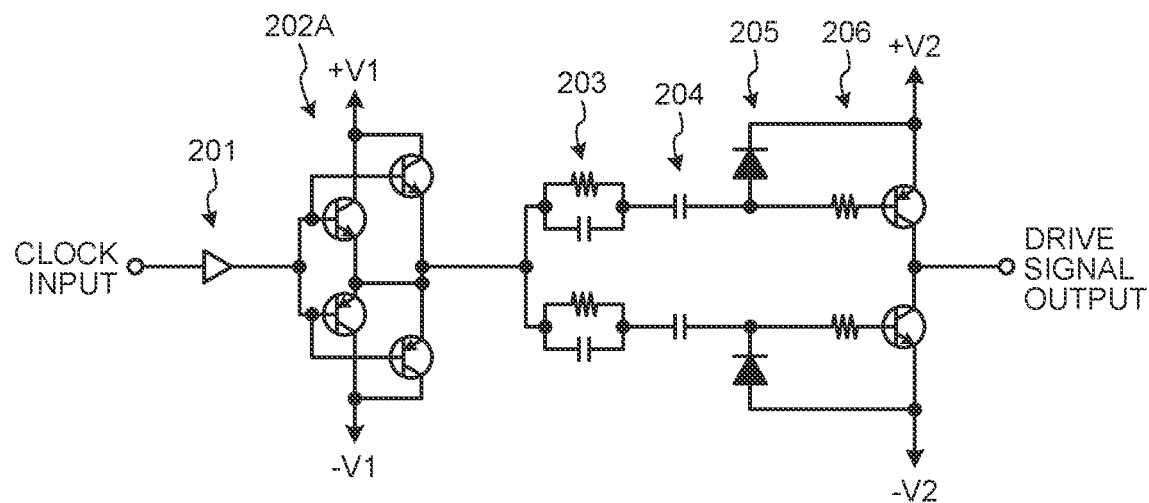
FIG. 31 is a diagram illustrating a circuit configuration for outputting a drive signal to an imaging element in a processing device, and is a diagram (part 1) illustrating a configuration according to the present application.
Figure 32:
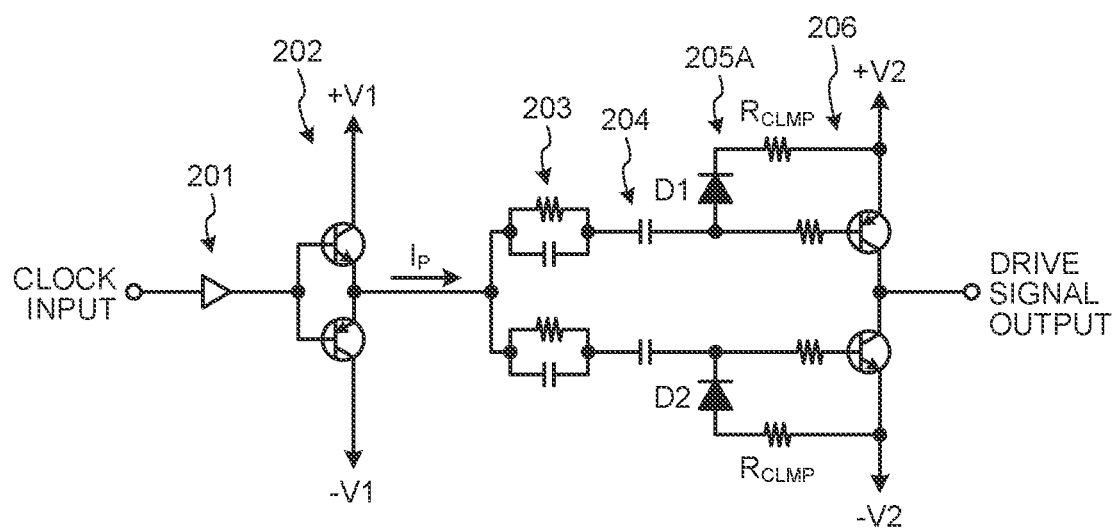
FIG. 32 is a diagram illustrating a circuit configuration for outputting a drive signal to an imaging element in a processing device, and is a diagram (part 2) illustrating a configuration according to the present application.

Here, the output of the drive signal to the imaging element 244 in the processing device 4 will be described with reference to FIGS. 30 to 32. FIG. 30 is a diagram illustrating a circuit configuration for outputting a drive signal to an imaging element in a processing device, and is a diagram illustrating a conventional configuration. FIGS. 31 and 32 are diagrams for explaining a circuit configuration for outputting a drive signal to an imaging element in a processing device, and are diagrams illustrating a configuration according to the present application.

Conventionally, a processing device generates and outputs a drive signal of the imaging element 244 with an input of a clock signal as a trigger. A generation circuit that generates the drive signal includes an AC logic unit 201, a push-pull circuit unit 202, a peaking circuit unit 203, a C coupling unit 204, a clamp circuit unit 205, and a drive circuit unit 206 (see FIG. 30).

The AC logic unit 201 receives an input of a clock signal.

The push-pull circuit unit 202 includes an NPN transistor and a PNP transistor. In the push-pull circuit unit 202, when an input voltage is +V1, the NPN transistor is turned on, the PNP transistor is turned off, and an output voltage is +(H). On the other hand, in the push-pull circuit unit 202, when the input voltage is -V1, the NPN transistor is turned off, the PNP transistor is turned on, and the output voltage is -(L).

The peaking circuit unit 203 performs processing of giving a peak to an edge portion of the waveform of the input signal.

The C coupling unit 204 is configured using a capacitor, and an AC signal passes therethrough.

The clamp circuit unit 205 includes two diodes and protects the circuit from overvoltage or the like. In the clamp circuit unit 205, one diode clamps to one power supply (voltage: +V2), and the other diode clamps to the other power supply (voltage: -V2).

The drive circuit unit 206 is configured using a transistor, and outputs a signal output from the clamp circuit unit 205 to the outside (imaging element 244) as a drive signal.

In the conventional configuration, a peak current Ip flows through the output unit of the push-pull circuit unit 202 due to the load of the diode clamping circuit. Due to this peak current, it is necessary to select a device satisfying the absolute maximum rating of the transistor, and options of the device are limited.

Examples of a configuration that does not limit the options of devices include a configuration in which the push-pull circuit unit 202 is replaced with a push-pull circuit unit 202A (see FIG. 31).

The push-pull circuit unit 202A is formed by connecting two push-pull circuits including an KPN transistor and a PNP transistor in parallel. The push-pull circuit unit 202A can be a circuit that satisfies the rating by distributing the current flowing through the device alone.

Furthermore, as a configuration capable of suppressing an increase in a mounting area without limiting options of devices, for example, a configuration in which the clamp circuit unit 205 is replaced with a clamp circuit unit 205A (see FIG. 32) can be exemplified.

The clamp circuit unit 205A is provided with resistors $R_{CLMP}$ between one diode and one power supply and between the other diode and the other power supply. By providing the resistor $R_{CLMP}$, the peak current Ip flowing through the output unit of the push-pull circuit unit 202 can be reduced. With this configuration, it is possible to suppress a decrease in device options or increase options while maintaining the same mounting area as the conventional configuration illustrated in FIG. 30 and the like. The peak current Ip can be adjusted by adjusting the resistor $R_{CLMP}$.

As described above, the light source device according to the disclosure is useful for uniformly mixing the light from the plurality of light sources and emitting the light with suppressed illuminance unevenness.

According to the disclosure, there is an effect that light from the plurality of light sources can be uniformly mixed to emit light with suppressed illuminance unevenness.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source device comprising:
a first semiconductor light source configured to emit light;
a condenser lens configured to condense the light; and
a light guide having an incident surface, an emission surface and at least one flat reflecting inner surface, the light guide configured to guide the light from the incident surface to the emission surface while reflecting the light on the at least one flat reflecting inner surface,
wherein the condenser lens is configured such that the light, after being incident on the incident surface, is perpendicularly incident to the at least one flat reflecting inner surface in a cross-sectional view of the light guide, the cross-sectional view being orthogonal to a central axis direction of the light guide.

2. The light source device according to claim 1, wherein a first straight line orthogonal to the at least one flat reflecting inner surface passes through the first semiconductor light source in a plan view as viewed in the central axis direction.

3. The light source device according to claim 2, wherein the first straight line passes through a central axis of the light guide.

4. The light source device according to claim 2,
wherein the first semiconductor light source is arranged on a first circumference having a first diameter equal to or less than an effective diameter of the condenser lens.

5. The light source device according to claim 4, further comprising a second semiconductor light source arranged on the first circumference.

6. The light source device according to claim 5, further comprising a third semiconductor light source arranged on a second circumference having a second diameter different from the first diameter.

7. The light source device according to claim 6, wherein the second diameter is less than the first diameter.

8. The light source device according to claim 5, further comprising an illumination controller configured to:
(i) turn off the second semiconductor light source;
(ii) subsequent to (i), turn off the first semiconductor light source.

9. The light source device according to claim 5, wherein in the cross-sectional view of the light guide, the second semiconductor light source is arranged on a second straight line different from the first straight line.

10. The light source device according to claim 5, wherein the first and second semiconductor light sources are arranged on opposite sides of the light guide across a central axis of the light guide.

11. The light source device according to claim 4, further comprising:
a second semiconductor light source arranged on the first circumference;
wherein the first semiconductor light source is configured to emit first light in a first wavelength band; and
the second semiconductor light source is configured to emit second light in a second wavelength band different from the first wavelength band.

12. The light source device according to claim 2, further comprising:
a second semiconductor light source arranged on a second circumference smaller than the first circumference; and
wherein the second semiconductor light source has a second dimming resolution lower than a first dimming resolution of the first semiconductor light source.

13. The light source device according to claim 1, further comprising:
a second semiconductor light source arranged on the first circumference;
wherein the first semiconductor light source has a light distribution having a shape of an ellipse with a first direction,
the second semiconductor light source has a light distribution having a shape of an ellipse with a second direction, and
the first direction is perpendicular to the second direction in the cross-sectional view of the light guide.

14. The light source device according to claim 1, further comprising a holder configured to hold the first semiconductor light source.

15. The light source device according to claim 1, further comprising:
a holder configured to hold the first semiconductor light source,
wherein the first light source is arranged at a corner of the holder.

16. The light source device according to claim 1, wherein the light guide has a polygonal shape in the cross-sectional view, the polygonal shape having an other inner surface other than the at least one flat reflecting inner surface, the other inner surface opposing the at least one flat reflecting inner surface across a central axis of the light guide.

17. The light source device according to claim 16, wherein the polygonal shape is a prism shape.

18. The light source device according to claim 16, wherein the other inner surface is a flat inner surface.

19. The light source device according to claim 1,
wherein the condenser lens comprises a first condenser lens, and
the light guide comprises a first light guide, the incident surface comprises a first incident surface, the emission surface comprises a first emission surface, the at least one flat reflecting inner surface comprises a first flat reflecting inner surface,
the light source device further comprising:
a second semiconductor source configured to emit second light;
a second condenser lens configured to condense the second light; and
a second light guide having a second incident surface, a second emission surface and at least one second flat reflecting inner surface, the second light guide configured to guide the second light from the second incident surface to the second emission surface while reflecting the second light on the at least one second flat reflecting inner surface,
wherein the second light is configured to perpendicularly incident on the second incident surface with respect to the at least one second flat reflecting inner surface in a cross-sectional view of the second light guide.

20. A method of guiding light, the method comprising:
emitting light from a light source;
condensing the light emitted from the light source by a condenser lens;
directing the light from the condenser lens on an incident surface of a light guide;
subsequent to the directing, perpendicularly reflecting the light to an at least one flat reflecting inner surface of the light guide in a cross-sectional view of the light guide, the cross-sectional view being orthogonal to a central axis direction of the light guide; and
guiding the light incident on the incident surface to an emission surface of the light guide while reflecting the light on the at least one flat reflecting inner surface.

* * * * *